(12) United States Patent
Kawamura et al.

(10) Patent No.: US 9,064,303 B2
(45) Date of Patent: Jun. 23, 2015

(54) MAGNETIC RESONANCE IMAGING APPARATUS AND MAGNETIC RESONANCE IMAGING METHOD CONFIGURED TO CORRECT SPECIFIC REGION DATA BASED ON BENCHMARK SLICE

(75) Inventors: Miyuki Kawamura, Tokyo (JP); Masahiro Takizawa, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 180 days.

(21) Appl. No.: 13/823,232

(22) PCT Filed: Sep. 21, 2011

(86) PCT No.: PCT/JP2011/071410
§ 371 (c)(1), (2), (4) Date: Mar. 14, 2013

(87) PCT Pub. No.: WO2012/043311
PCT Pub. Date: Apr. 5, 2012

(65) Prior Publication Data
US 2013/0170727 A1 Jul. 4, 2013

(30) Foreign Application Priority Data

Sep. 27, 2010 (JP) ................................ 2010-215335

(51) Int. Cl.
| | |
|---|---|
| *G06K 9/00* | (2006.01) |
| *G06T 7/00* | (2006.01) |
| *A61B 5/00* | (2006.01) |
| *G01R 33/48* | (2006.01) |
(Continued)

(52) U.S. Cl.
CPC ..... *G06T 7/0012* (2013.01); *G06T 2207/10088* (2013.01); *A61B 5/055* (2013.01); *A61B 5/7207* (2013.01); *G01R 33/4824* (2013.01); *G01R 33/56509* (2013.01); *A61B 2576/00* (2013.01)

(58) Field of Classification Search
None
See application file for complete search history.

(56) References Cited

U.S. PATENT DOCUMENTS

| | | | | |
|---|---|---|---|---|
| 5,298,861 | A | * | 3/1994 | Sugimoto ..................... 324/306 |
| 5,946,425 | A | * | 8/1999 | Bove et al. ..................... 382/294 |

(Continued)

FOREIGN PATENT DOCUMENTS

| | | |
|---|---|---|
| JP | 2008-178592 | 8/2008 |
| JP | 2010-524622 | 7/2010 |

(Continued)

OTHER PUBLICATIONS

International Search Report in PCT/JP2011/071410.
(Continued)

*Primary Examiner* — Wenpeng Chen
(74) *Attorney, Agent, or Firm* — Cooper & Dunham LLP

(57) ABSTRACT

In multi-slice imaging of a magnetic resonance imaging apparatus based on a non-Cartesian sampling method in which an overlap portion is generated in k space, stable body movement correction is realized at high speed. In order to do so, the rotation and translation of an object is detected for each specific region (in the case of a hybrid radial method, each blade) using a most characteristic slice in the imaging region, and the detected body movement is used for body movement correction of the specific region in all slices. The slice used for correction may be determined using a mathematical analysis result, such as correlation. In addition, data collection and correction processing may be performed in parallel.

12 Claims, 20 Drawing Sheets

(51) Int. Cl.
*A61B 5/055* (2006.01)
*G01R 33/565* (2006.01)

(56) References Cited

U.S. PATENT DOCUMENTS

| | | | |
|---|---|---|---|
| 6,496,560 B1* | 12/2002 | Lin et al. | 378/62 |
| 6,512,807 B1* | 1/2003 | Pohlman et al. | 378/4 |
| 6,745,066 B1* | 6/2004 | Lin et al. | 600/425 |
| 7,423,430 B1* | 9/2008 | Sharif et al. | 324/309 |
| 2006/0224062 A1* | 10/2006 | Aggarwal et al. | 600/413 |
| 2007/0182411 A1* | 8/2007 | Bammer et al. | 324/307 |
| 2008/0180098 A1* | 7/2008 | Takei | 324/309 |
| 2008/0317315 A1* | 12/2008 | Stemmer | 382/131 |
| 2009/0115794 A1* | 5/2009 | Fukuta | 345/581 |
| 2010/0141253 A1* | 6/2010 | Takizawa et al. | 324/309 |
| 2010/0215238 A1* | 8/2010 | Lu et al. | 382/131 |
| 2010/0290682 A1* | 11/2010 | Itagaki | 382/131 |
| 2011/0234222 A1* | 9/2011 | Frahm et al. | 324/309 |

FOREIGN PATENT DOCUMENTS

| | | | | |
|---|---|---|---|---|
| WO | WO 2005/023108 A1 | 3/2005 | | |
| WO | WO 2005023108 A1 * | 3/2005 | ............. | A61B 5/055 |
| WO | WO 2006/077715 A1 | 7/2006 | | |
| WO | WO 2008/132659 A2 | 11/2008 | | |
| WO | WO 2008132659 A2 * | 11/2008 | ........... | G01R 33/561 |
| WO | WO 2008152937 A1 * | 12/2008 | | |
| WO | WO 2009/093517 A1 | 7/2009 | | |
| WO | WO 2009093517 A1 * | 7/2009 | ........... | G01R 33/561 |

OTHER PUBLICATIONS

J. Pipe, "Periodically Rotated Overlapping ParallEL Lines with Enhanced Reconstruction (PROPELLER) MRI; Application to Motion Correction", Proc. Intl. Soc. Mag. Reson. Med., 1999, 242.

* cited by examiner

* 1 : EXTRACTION  * 2 : CORRECTION  * 3 : RECONSTRUCTION

FIG.11
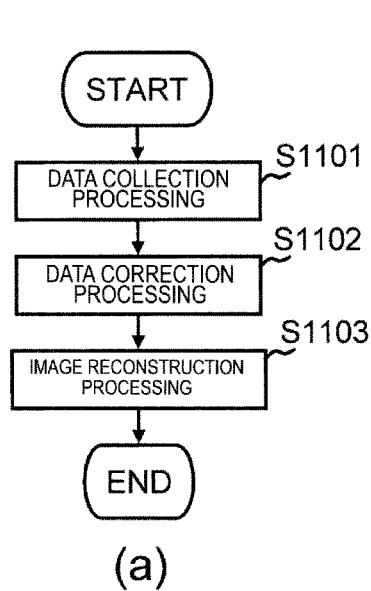
(a)
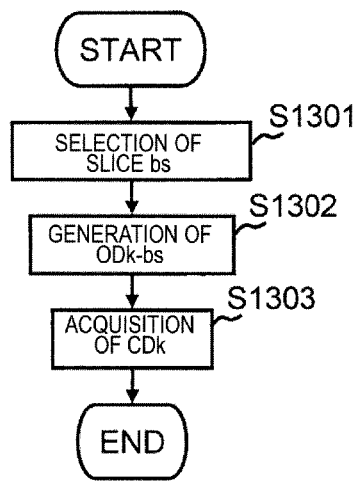
(c)
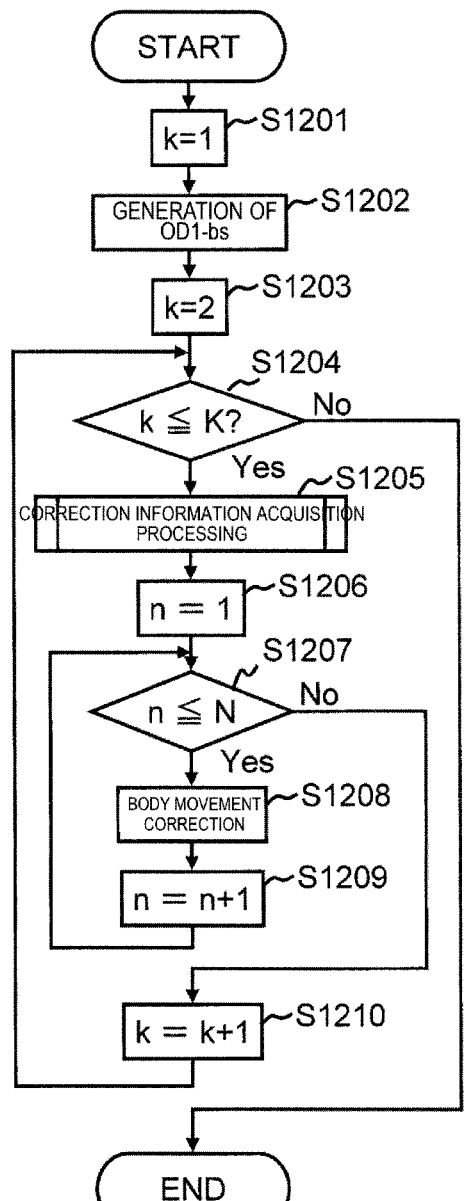
(b)

FIG.15 --Prior Art--

MAGNETIC RESONANCE IMAGING APPARATUS AND MAGNETIC RESONANCE IMAGING METHOD CONFIGURED TO CORRECT SPECIFIC REGION DATA BASED ON BENCHMARK SLICE

TECHNICAL FIELD

The present invention relates to a magnetic resonance imaging (hereinafter, referred to as an "MRI") apparatus and in particular, to a body movement correction technique in a non-Cartesian sampling method.

BACKGROUND ART

The MRI apparatus is an apparatus that measures an NMR signal generated by the object, especially, the spins of nuclei which form human tissue, and images the shapes or functions of the head, abdomen, limbs, and the like in a two-dimensional manner or in a three-dimensional manner. In the imaging, different phase encoding and different frequency encoding are given to NMR signals according to the gradient magnetic field, and the NMR signals are measured as time series data. The measured NMR signals are reconstructed as an image by a two-dimensional or three-dimensional Fourier transform.

If an object moves during the measurement of NMR signals, body movement artifacts are caused in the reconstructed image. A non-Cartesian sampling method is known as an effective method to suppress the occurrence of body movement artifacts. Examples of a non-Cartesian sampling method include a radial method (for example, refer to NPL 1), which acquires echo signals required for the reconstruction of one image by performing sampling radially while changing the rotation angle with approximately one point (generally, the origin) of measurement space as the rotation center, and a hybrid radial method (for example, refer to NPL 2 and NPL 3), which is a combination of the radial method and phase encoding and which divides the measurement space into a plurality of different blades in a sampling direction, samples the blades, and performs phase encoding within the blades.

In particular, the hybrid radial method is a method of filling k space while rotating a plurality of k-trajectories (trajectories of k space; blades), which are obtained in one repetition time (TR) by the fast spin echo (FSE) method, every TR. In the hybrid radial method, each blade certainly fills the center of k space. There is a technique of detecting the rotation or translation of the object using the overlap portion and correcting the body movement (for example, refer to NPL 3).

In the technique disclosed in NPL 3, however, the spatial resolution of an image for correction, which is generated from the overlap portion of k space used to detect body movement, is generally lower than that of a diagnostic image used for diagnostic purposes. For this reason, characteristic points, such as a structure, may not be detected in the image for correction. In particular, at the slice position where the cross section is almost circular, such as the head, the body movement of an object may be incorrectly detected even if the object does not actually move and accordingly an incorrect image for correction may be generated.

In multi-slice imaging, there is a technique for removing a slice from which an incorrect image for correction has been generated (hereinafter, referred to as an incorrect slice) and recalculating a correction parameter of the removed incorrect slice from correction parameters of other slices (for example, refer to PTL 1).

PATENT LITERATURE

[PTL 1] JP-A-2009-131613

CITATION LIST

Non Patent Literature

[NPL 1] Magnetic Resonance in Medicine 28: 275-289 (1992). Projection Reconstruction Techniques for Reduction of Motion Effects in MRI. G. H. Glover, J. M. Pauly.

[NPL 2] Magnetic Resonance in Medicine 42: 963-969 (1999). Motion Correction With PROPELLER MRI: Application to Head Motion and Free-Breathing Cardiac Imaging. James G. Pipe.

[NPL 3] Magnetic Resonance in Medicine 97: 42-52 (2002). Multishot Diffusion-Weighted FSE Using PROPELLER MRI. James G. Pipe, et. Al.

SUMMARY OF INVENTION

Technical Problem

In the technique disclosed in PTL 1, the operator subjectively determines and removes an incorrect slice from the resulting image. Accordingly, an incorrect slice is not necessarily determined with high accuracy. In addition, if a slice remains that should have been originally removed as an incorrect slice, an incorrect value remains since the slice is also used in recalculation of the correction parameter. Accordingly, there is a possibility that the correction accuracy will not be improved. In addition, since a resulting image needs to be generated once, it is necessary to perform correction processing as usual. As a result, the processing becomes complicated, and the processing time is required.

The present invention has been made in view of the above-described situation, and it is an object of the present invention to provide a technique for realizing stable body movement correction at high speed in multi-slice imaging based on a non-Cartesian sampling method in which an overlap portion is generated in k space.

Solution to Problem

In the present invention, body movement (rotation and translation) of an object is detected for each specific region in the case of the hybrid radial method, each blade) using a most characteristic slice in the imaging region, and the detected body movement is used for body movement correction of the specific region in all slices. The slice used for correction may be determined using a result of a mathematical analysis, such as correlation. In addition, data collection and correction processing may be performed in parallel.

Specifically, there is provided a magnetic resonance imaging apparatus that acquires an image of each slice of an object on the basis of magnetic resonance signals measured from a plurality of slices of the object arranged in a static magnetic field. The magnetic resonance imaging apparatus includes: a data collection unit that collects a magnetic resonance signal corresponding to each specific region as specific region data by rotating a specific region, which includes an origin of k space and a vicinity of the origin, around the origin; a data correction unit that corrects the specific region data to generate corrected specific region data; and an image reconstruction unit that reconstructs an image from the corrected specific region data. The data correction unit sets one of the plurality of slices as a benchmark slice, detects body movement of the object, which occurs between measurement of a reference specific region as a reference of the plurality of specific regions and measurement of other specific regions excluding the reference specific region, in the benchmark slice, corrects specific region data of the other specific regions in all slices so as to eliminate an influence of the detected body movement on an image, and sets specific region data of the reference specific region and specific region data after correction of the other specific regions as the corrected specific region data in each slice.

In addition, there is provided a magnetic resonance imaging method of acquiring an image of each slice of an object on the basis of magnetic resonance signals measured from a plurality of slices of the object arranged in a static magnetic field. The magnetic resonance imaging method includes: a data collection step of collecting a magnetic resonance signal corresponding to each specific region as specific region data by rotating a specific region, which includes an origin of k space and a vicinity of the origin, around the origin; a data correction step of correcting the specific region data to generate corrected data; and an image reconstruction step of reconstructing an image from the corrected data. The data correction step includes a correction information calculation step of calculating as correction information an amount of body movement of the object, which occurs between measurement of a reference specific region as a reference of the plurality of specific regions and measurement of other specific regions excluding the reference specific region, in a benchmark slice as a reference and a correction step of correcting data of the other specific regions for all slices using the calculated correction information of each of the other specific regions.

Advantageous Effects of Invention

According to the present invention, it is possible to provide an MRI apparatus capable of performing stable body movement correction in multi-slice imaging based on a non-Cartesian sampling method in which an overlap portion is generated in k space.

BRIEF DESCRIPTION OF DRAWINGS

FIG. 11(a) is a flow chart of imaging processing of the first embodiment, FIG. 11(b) is a flow chart of data correction processing of the first embodiment, and FIG. 11(c) is a flow chart of correction information acquisition processing of the first embodiment.

DESCRIPTION OF EMBODIMENTS

First Embodiment

Figure 1:
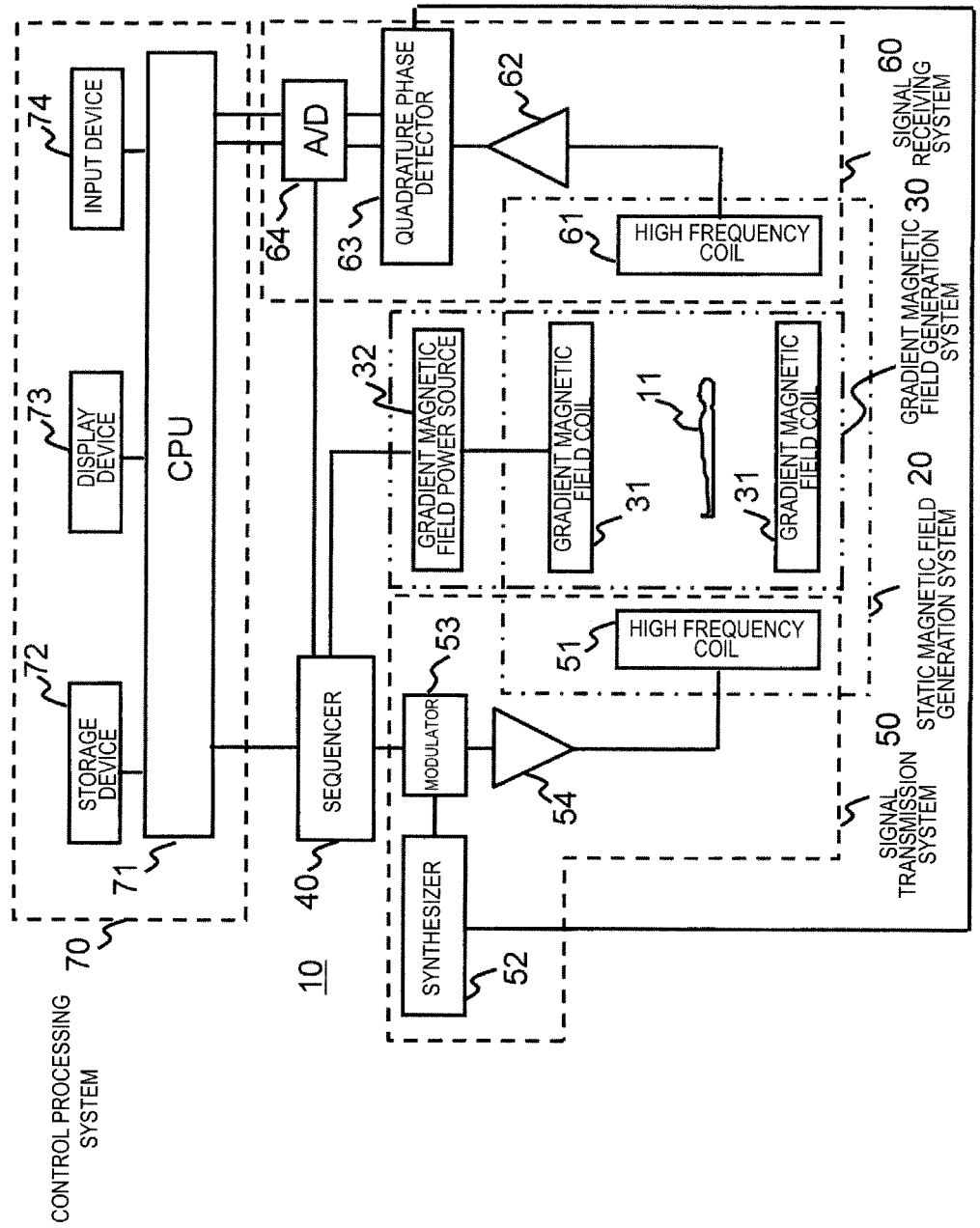
FIG. 1 is a block diagram of an MRI apparatus of a first embodiment.

Hereinafter, a first embodiment to which the present invention is applied will be described. Hereinafter, in all drawings for explaining the embodiments of the present invention, the same reference numerals are given to elements having the same functions, and repeated explanation thereof will be omitted.

First, the outline of an example of an MRI apparatus of the present embodiment will be described. FIG. 1 is a block diagram showing the overall configuration of an MRI apparatus 10 of the present embodiment. The MRI apparatus 10 of the present embodiment acquires a tomographic image of an object 11 using an NMR phenomenon. As shown in FIG. 1, the MRI apparatus 10 includes a static magnetic field generation system 20, a gradient magnetic field generation system 30, a signal transmission system 50, a signal receiving system 60, a control processing system 70, and a sequencer 40.

The static magnetic field generation system 20 generates a uniform static magnetic field in the space around the object 11 in a direction perpendicular to the body axis in the case of a vertical magnetic field method and in the body axis direction in the case of a horizontal magnetic field method, and includes a permanent magnet type, normal conduction type, or superconducting type static magnetic field generator disposed around the object 11.

The gradient magnetic field generation system 30 includes gradient magnetic field coils 31 wound in three axial directions of X, Y, and Z, which are the coordinate system (stationary coordinate system) of the MRI apparatus 10, and a gradient magnetic field power source 32 which drives each gradient magnetic field coil, and applies gradient magnetic fields Gx, Gy, and Gz in the three axial directions of X, Y, and Z by driving the gradient magnetic field power source 32 of each gradient magnetic field coil 31 according to a command from the sequencer 40, which will be described later.

The signal transmission system 50 emits a high frequency magnetic field pulse (hereinafter, referred to as an "RF pulse") to the object 11 in order to cause nuclear magnetic resonance in the nuclear spins of atoms which form the body tissue of the object 11, and includes a high frequency oscillator (synthesizer) 52, a modulator 53, a high frequency amplifier 54, and a transmission-side high frequency coil transmission coil) 51. The high frequency oscillator 52 generates an RF pulse and outputs it at the timing based on a command from the sequencer 40. The modulator 53 performs amplitude modulation of the output RF pulse, and the high frequency amplifier 54 amplifies the amplitude-modulated RF pulse and supplies it to the transmission coil 51 disposed near the object 11. The transmission coil 51 emits the supplied RF pulse to the object 11.

The signal receiving system 60 detects a nuclear magnetic resonance signal (an echo signal, an NMR signal) emitted by the nuclear magnetic resonance of the spins of nuclei, which form the body tissue of the object 11, and includes a receiving-side high frequency coil (receiving coil) 61, a signal amplifier 62, a quadrature phase detector 63, and an AD converter 64. The receiving coil 61 is disposed near the object 11, and detects an NMR signal of the response from the object 11 that is induced by the electromagnetic wave emitted from the transmission coil 51. The detected NMR signal is amplified by the signal amplifier 62 and is then divided into two orthogonal signals by the quadrature phase detector 63 at the timing based on the command from the sequencer 40. Each of the orthogonal signals is converted into the digital amount by the A/D converter 64 and is transmitted to the control processing system 70.

The sequencer 40 repeatedly applies an RF pulse and a gradient magnetic field pulse according to the predetermined pulse sequence. In addition, the pulse sequence describes the timing or the strength of a high frequency magnetic field, a gradient magnetic field, and signal reception, and is stored in advance in the control processing system 70. The sequencer 40 operates according to the instructions from the control processing system 70, and transmits various commands, which are required for data collection of a tomographic image of the object 11, to the signal transmission system 50, the gradient magnetic field generation system 30, and the signal receiving system 60.

The control processing system 70 performs overall control of the MRI apparatus 10, various kinds of data processing, display and storage of processing results, and the like, and includes a CPU 71, a storage device 72, a display device 73, and an input device 74. The storage device 72 is formed by an external storage device, such as a hard disk, an optical disc, and a magnetic disk. The display device 73 is a CRT, a liquid crystal display device, or the like. The input device 74 is an interface for the input of various kinds of control information of the MRI apparatus 10 or control information of processing performed in the control processing system 70. For example, the input device 74 includes a track ball or a mouse and a keyboard. The input device 74 is disposed near the display device 73. The operator interactively inputs instructions and data, which are required for various kinds of processing of the MRI apparatus 10, through the input device 74 while observing the display device 73.

The CPU 71 realizes the control of the operation of the MRI apparatus 10 and each process, such as various kinds of data processing, of the control processing system 70 by executing a program stored in advance in the storage device 72 according to the instruction input by the operator. For example, when the data from the signal receiving system 60 is input to the control processing system 70, the CPU 71 executes processing, such as signal processing and image reconstruction, and displays a tomographic image of the object 11, which is the result, on the display device 73 and also records it in the storage device 72.

The transmission coil 11 and the gradient magnetic field coil 31 are provided in the static magnetic field space of the static magnetic field generation system 20, in which the object 11 is inserted, so as to face the object 11 in the case of a vertical magnetic field method and so as to surround the object 11 in the case of a horizontal magnetic field method. In addition, the receiving coil 61 is provided so as to face or surround the object 11.

Currently, a nuclide imaged by an MRI apparatus, which is widely used clinically, is a hydrogen nucleus (proton) which is a main constituent material of the object 11. In the MRI apparatus 10, the shapes or functions of the head, abdomen, limbs, and the like of the human body are imaged in a two-dimensional or three-dimensional manner by performing imaging of the spatial distribution of the proton density or the information regarding the spatial distribution of the relaxation time of the excited state.

As described above, as a sampling method to suppress the occurrence of body movement artifacts, there is a non-Cartesian sampling method. Examples of the non-Cartesian sampling method include a radial sampling method, a hybrid radial method, and a spiral method.

In particular, the hybrid radial method is a combination of a radial method and phase encoding. Specifically, an echo signal corresponding to each blade is measured as blade data (specific region data) by rotating a blade (specific region) which has a plurality of parallel trajectories in k space, around the origin of k space, that is, setting respective blades to have different angles in k space. Within each blade, a phase encoding pulse is applied for one rotation angle in the same manner as in the case of normal measurement (measurement based on the Cartesian sampling method), thereby obtaining a plurality of echo signals. By repeating this every rotation angle (that is, every blade), all echo signals required for reconstruction of one image are acquired. In the hybrid radial method, a low spatial frequency region of k space is repeatedly measured. Accordingly, since a signal variation due to body movement can be extracted by using the overlap portion, body movement can be corrected.

In addition, the spiral method is a technique of acquiring echo signals required for reconstructing one image by performing spiral sampling while changing the rotation angle and the radius of rotation with approximately one point (generally, the origin) of k space as the rotation center. The spiral method is applied as a high-speed imaging method since less time is wasted when filling the k space and the data can be efficiently collected. In addition, the spiral method is characterized in that a gradient magnetic field pulse waveform used when reading an echo signal is not a trapezoidal wave but a combination of a sine wave and a cosine wave and accordingly, the gradient magnetic field pulse waveform is efficient for the gradient magnetic field system and there is less noise when applying a gradient magnetic field. Also in this spiral method, it is possible to measure the low spatial frequency region of k space repeatedly. Accordingly, since a signal variation due to body movement can be extracted, body movement can be corrected.

In the present embodiment, body movement is corrected by performing sampling using these non-Cartesian sampling methods and extracting the variation due to body movement using the data of the low spatial frequency region of k space obtained by repeated measurement. Therefore, both the hybrid radial method and the spiral method can be applied.

However, in the present embodiment, an example of the case where the hybrid radial method is used will be described hereinafter.

Figure 2:
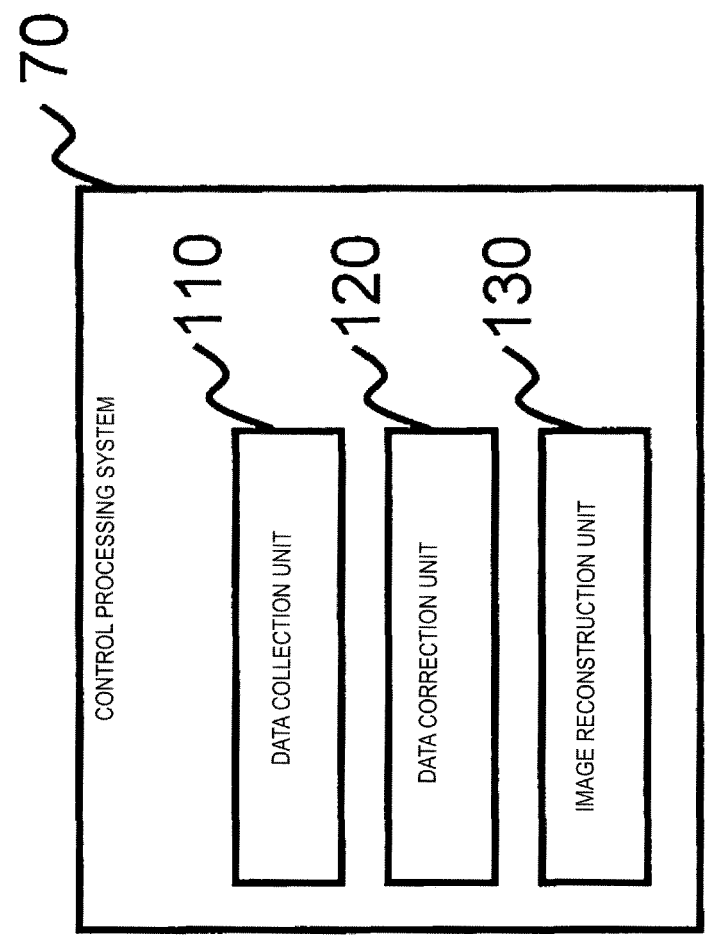
FIG. 2 is a functional block diagram of a control processing system of the first embodiment.

FIG. 2 shows a functional block diagram of the control processing system 70 of the present embodiment. As shown in this drawing, the control processing system 70 of the present embodiment executes the above-described body movement correction by performing multi-slice imaging based on the hybrid radial method, thereby reconstructing an image. For this reason, the control processing system 70 of the present embodiment includes a data collection unit 110 that collects echo signals and arranges the echo signals in k space, a data correction unit 120 that performs body movement correction for the data arranged in k space, and an image reconstruction unit 130 that reconstructs an image from the data after correction. Each of these functions is realized when the CPU 71 executes a program stored in advance in the storage device 72 as described above.

The data collection unit 110 collects echo signals by sampling k space for each of a plurality of slices using the hybrid radial method as described above (multi-slice imaging). In the present embodiment, the collected echo signals are arranged in k space prepared for each blade and each slice. Hereinafter, the echo signals arranged in the blade region of k space are called blade data.

Figure 3:
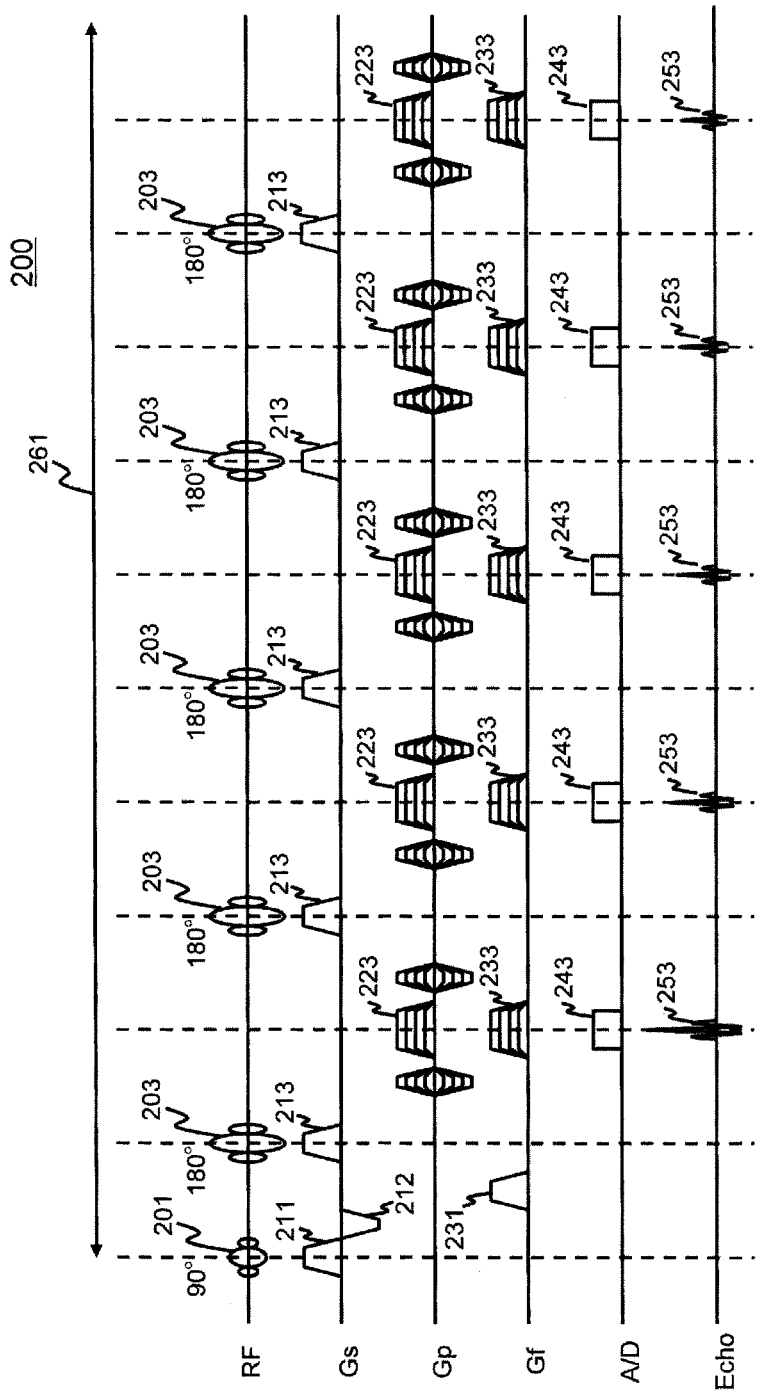
FIG. 3 is a pulse sequence diagram of a hybrid radial method.

Here, FIG. 3 shows an example of a pulse sequence 200 of the SE-based hybrid radial method which is executed when the data collection unit 110 of the present embodiment performs blade data collection. In this drawing, RF, Gs, Gp, Gf, AD, and Echo indicate axes of an RF pulse, a slice gradient magnetic field, a first readout gradient magnetic field, a second readout gradient magnetic field, AD conversion, and an echo signal, respectively.

First, an excitation RF pulse 201 for providing a high frequency magnetic field to the spins within the imaging plane and a slice selection gradient magnetic field pulse 211 are applied. A slice re-phase pulse 212 for returning the phase of the spins diffused by the slice selection gradient magnetic field pulse 211 and a readout dephase gradient magnetic field pulse 231, which distributes the phase of the spins in advance in order to generate an echo signal, are applied immediately after the application of the slice selection gradient magnetic field pulse 211. Then, a reverse RF pulse 203 for reversing the spins within the slice plane is repeatedly applied. Then, a slice selection gradient magnetic field pulse 213 for selecting a slice, a first readout gradient magnetic field pulse 223, and a second readout gradient magnetic field pulse 233 are applied for each application of the reverse RF pulse 203, and an echo signal 253 is collected at the timing of a sampling window 243.

Here, an example of collecting five groups of the echo signals 253 in every excitation RF pulse 201 is shown (the reverse RE pulse 203 is applied 5 times). In this case, a k space region filled with the groups of the echo signals 253 collected in every excitation RE pulse 201 is a blade. Assuming that the readout direction and the phase encoding direction in a blade are Kx' and Ky', respectively, the first and second readout gradient magnetic field pulses 221 and 232 are controlled such that the echo signals 253 are collected from −Ky' to Ky'.

In addition, in order to measure each blade at different rotation angles of k space, all groups of the required echo signals 253 are collected by repeatedly executing this sequence while changing the amplitudes of the readout dephase gradient magnetic field pulse 231 and the readout gradient magnetic field pulses 223 and 233 at intervals of time 261.

Figure 4:
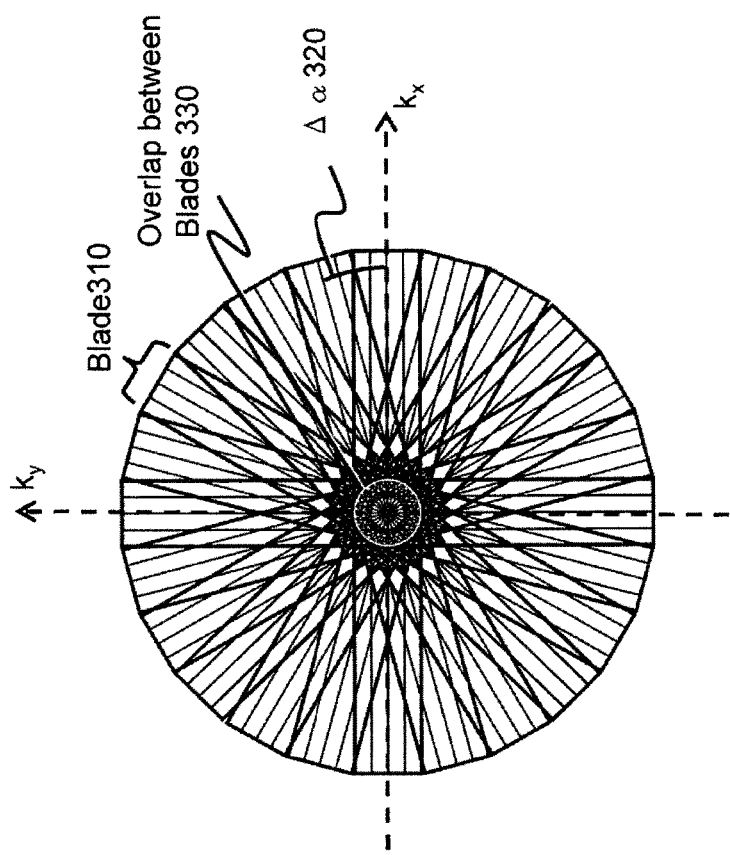
FIG. 4 is an explanatory diagram for explaining k space in a symmetrical FOV using the hybrid radial method.

FIG. 4 shows a state where echo signals collected by this hybrid radial method are arranged in k space. In this drawing, a case where the angle of the measurement trajectory for the coordinate axes (kx-ky) of k space is divided into 12 different blades 310 to measure the k space is illustrated. The central angle between the adjoining blades 310 is set to $\Delta\alpha(=\pi/12)$ 320. In addition, this is an example where within each blade 310, five echo signals 253 with different amounts of phase encoding are acquired.

Figure 5:
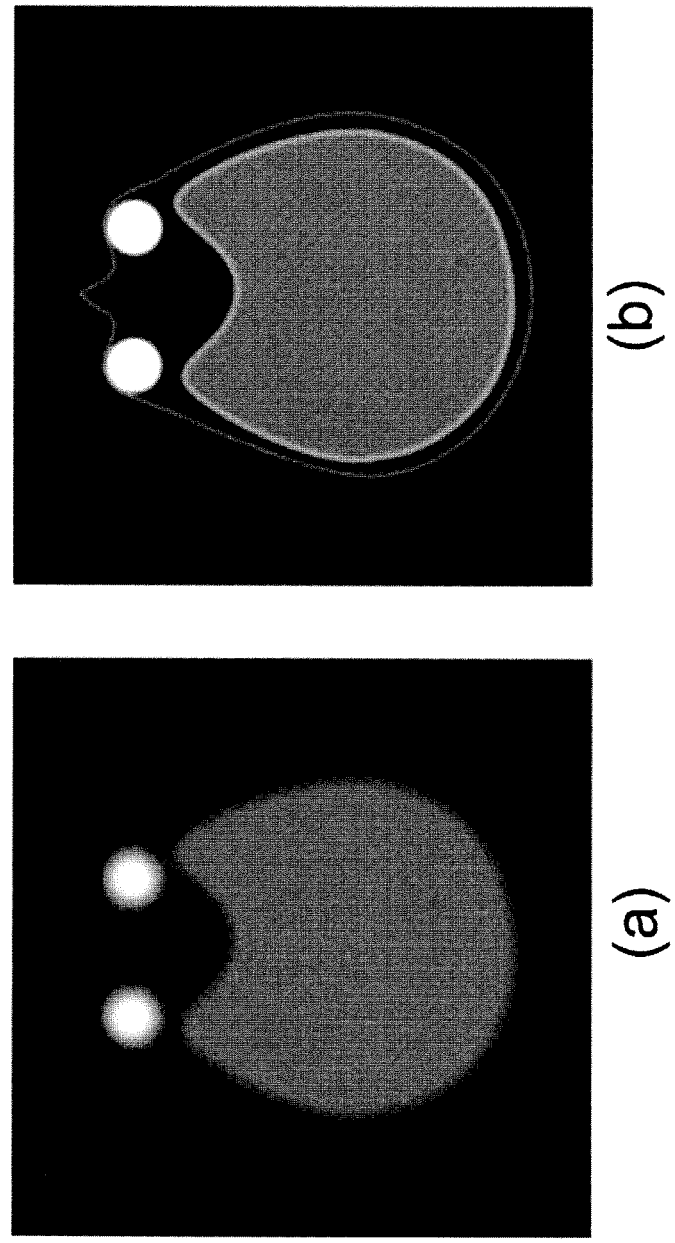
FIG. 5(a) is an explanatory diagram for explaining an image reconstructed from the data of an overlap portion of echo signals collected by the hybrid radial method.
FIG. 5(b) is an explanatory diagram for explaining an image reconstructed from all items of the blade data.

As shown in this drawing, in the case of sampling using the hybrid radial method, an overlap portion (Overlap between Blades) 330 in which sampling regions of the blades 310 overlap each other is generated. Since this overlap portion 330 is a low spatial frequency region of k space, it is possible to generate an image with low spatial resolution to determine the image contrast or the signal strength. Here, FIG. 5(a) shows an image reconstructed from the data of the overlap portion 330, and FIG. 5(b) shows an image reconstructed from all data items of the blade 310.

In addition, assuming that the number of blades for dividing and measuring the k space is K, the number of echo trains in one blade is L (that is, the diameter of the overlap portion 330), and the effective matrix is M, the relationship of K, L, and M is expressed as in Expression (1).

[Expression 1]

$$LK = M\frac{\pi}{2} \qquad (1)$$

Figure 6:
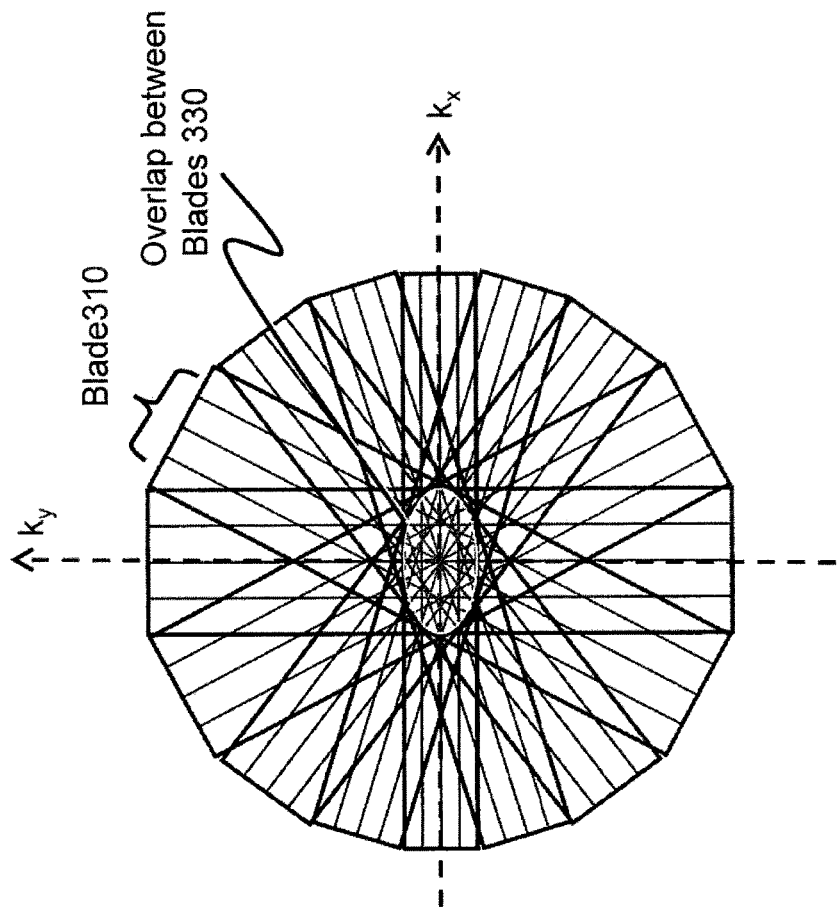
FIG. 6 is an explanatory diagram for explaining k space in an asymmetrical FOV using the hybrid radial method.

In addition, FIG. 4 schematically shows the data arrangement of k space when the imaging field of view ((FOV) is symmetrical, and FIG. 6 shows the data arrangement when the FOV is asymmetrical.

The data correction unit 120 of the present embodiment calculates the correction information of each blade and corrects the blade data using the above-described overlap portion. The correction information to be calculated is the amount of body movement of the object from the reference point of time of blade measurement. The amount of body movement is detected using the fact that data (after gridding processing) of the above-described overlap portion 330 of each blade is the same k space coordinate value if there is no body movement.

Figure 7:
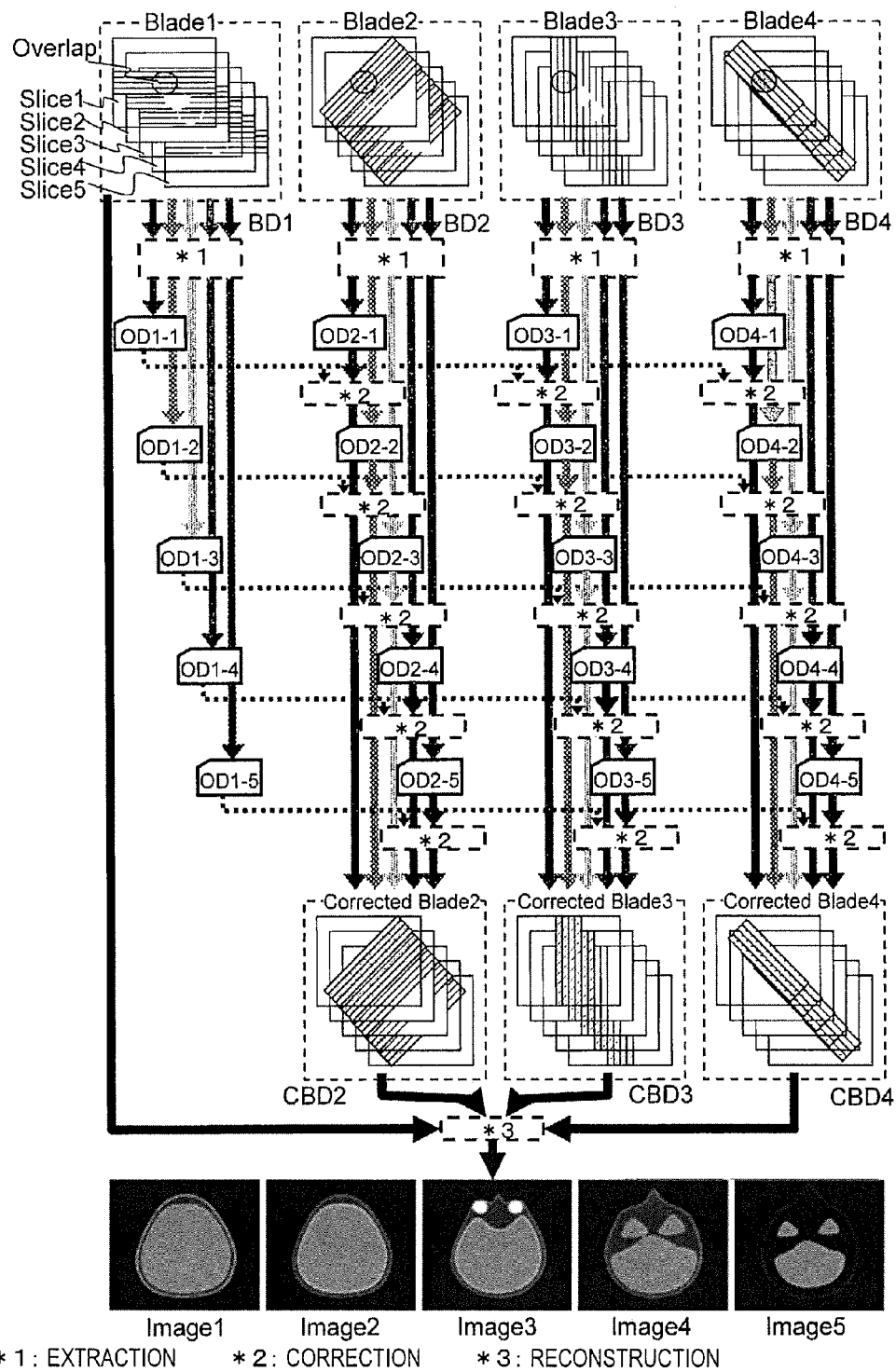
FIG. 7 is an explanatory diagram for explaining the flow of conventional correction processing.

Prior to explaining the correction processing of the data correction unit 120 of the present embodiment in detail, body movement correction at the time of multi-slice imaging based on the normal hybrid radial method will be described. FIG. 7 is a diagram for explaining the procedure of typical correction processing for correcting the body movement. Here, a case where the number of slices is 5 and the number of blades is 4 is shown as an example. In addition, the number of echo signals in each blade is set to 5. In addition, in order to simplify the explanation, it is assumed herein that each item of blade data is subject to gridding processing in advance when all echo signals 253 in the blade are aligned. However, the gridding processing may also be performed during the correction of the body movement.

In addition, consecutive slice numbers and consecutive blade numbers starting from 1, which uniquely specify blades and slices, are given to the blades and the slices. In addition, a slid with a slice number of k is called a slice k, and a blade with a blade number of n is called a blade n. That is, five slices are called a slice 1 (Slice1), a slice 2 (Slice2), a slice 3 (Slice3), a slice 4 (Slice4), and a slice 5 (Slice5), and four blades are called a blade 1 (Blade1), a blade 2 (Blade2), a blade 3 (Blade3), and a blade 4 (Blade4).

In addition, the blade 1 is assumed to be a blade used as a reference of correction (reference blade). First, in the blade 1, for each slice, blade data (overlap data) of an overlap region (overlap portion; Overlap) that overlaps other blades is extracted from the blade data (BD) 1, and the extracted data is set as reference data. The reference data of each slice is called OD1-1, OD1-2, OD1-3, OD1-4, and OD1-5.

Then, in the blade 2, similarly for the blade 1, overlap data is extracted from blade data (BD2) for each slice, and the extracted data is set as object data. The object data of each slice is called OD2-1, OD2-2, OD2-3, OD2-4, and OD2-5.

In addition, for each slice, the amount of body movement (the amount of rotation and the amount of translation) of the object is detected from the reference data and the object data. Then, the blade data of the slice is corrected using the detected amount of body movement so that the influence of the body movement on the image is eliminated, thereby obtaining corrected blade data (CBD) 2. In addition, details of the calculation of correction information and a correction method will be described later.

Similarly for the blades 3 and 4, overlap data is extracted from the blade data (BD3, BD4) for each slice, and the extracted data is set as object data (OD3-1, OD3-2, OD3-3, and OD3-4, OD3-5, OD4-1, OD4-2, OD4-3, OD4-4, and OD4-5).

Then, for each slice, the amount of body movement is detected from the reference data and the object data and the blade data of the slice is corrected, thereby obtaining corrected blade data (CBD3, CBD4).

The blade data (BD1) of each slice of the blade 1 and the corrected blade data of respective slices of other obtained blades (CBD2, CBD3, CBD4) are combined for each slice, and reconstruction processing, such as a Fourier transform, is performed on the combined blade data for each slice, thereby obtaining reconstructed images (Image1, Image2, Image3, Image4, Image5) of each slice.

Next, details of body movement correction in one slice of the normal hybrid radial method will be described with reference to FIG. 8. Similarly in FIG. 7, it is also assumed herein that the number of blades is 4, the number of echo signals in each blade is 5, and the blade 1 is a reference blade.

Generally, body movement correction is performed for rotation and translation among the movement of the object (body movement) occurring between the measurement of the reference blade and the measurement of other blades. The amount of rotation based on the rotation and the amount of translation based on the translation are detected for each blade, and correction is performed to eliminate these.

First, acquired echo signals are arranged in k space and are subjected to gridding processing. Then, for each blade, data (overlap data) of an overlap portion of the blade data (BD) is extracted after gridding processing. Here, overlap data of the blade 1 is set as the reference data (OD1), and overlap data of other blades is set as object data (OD2, OD3, OD4).

First, rotation correction is performed. In the rotation correction, the amount of rotation is detected first. Here, the rotation angle of each item of the object data (OD2, OD3, OD4) with the reference data (OD1) as a reference is calculated using the fact that the rotation in image space becomes the rotation of the absolute value of k space as it is. Then, the calculated rotation angle is set as the amount of rotation of each blade, and the blade data (BD) is corrected so as to cancel the amount of rotation.

Then, translation correction is performed. In the translation correction, the amount of translation is detected first. The amount of translation can be detected as a phase difference between overlap data. Therefore, the phase difference between the reference data (OD1) and the object data (OD2, OD3, OD4) is calculated, and this is set as the amount of translation. Then, the blade data after rotation correction is corrected so as to cancel the calculated phase difference (the amount of translation), thereby obtaining the corrected blade data (CBD).

After the body movement correction of blades other than the blade 1 as a reference ends as described above, blade data is generated by performing a combination (signal combination) of the blade data (BD) of the blade 1 and the corrected blade data (CBD) of the blades 2 to 4. A Fourier transform (FFT) of the blade data is performed to obtain a reconstructed image.

In addition, the amount of rotation may be detected by performing correlation processing in an image with low spatial resolution generated by performing a Fourier transform of the reference data and the object data. In addition, the amount of translation may also be similarly calculated using an image with low spatial resolution generated by performing a Fourier transform of the reference data and the object data.

That is, the pixel deviation between images is calculated by correlation processing, the phase difference in k space is calculated on the basis of the calculated pixel deviation, and this is set as the amount of translation described above. In the present embodiment, any method may be adopted.

Next, the procedure of correction processing for correcting the body movement using the data correction unit 120 of the present embodiment will be described. The data correction unit 120 of the present embodiment detects the above-described amount of body movement (the amount of rotational movement and the amount of translation) as correction information, for each blade, between the benchmark slice of the reference blade set in advance and the benchmark slice of other blades. Then, this correction information is applied to all slices for each blade to perform correction.

Figure 9:
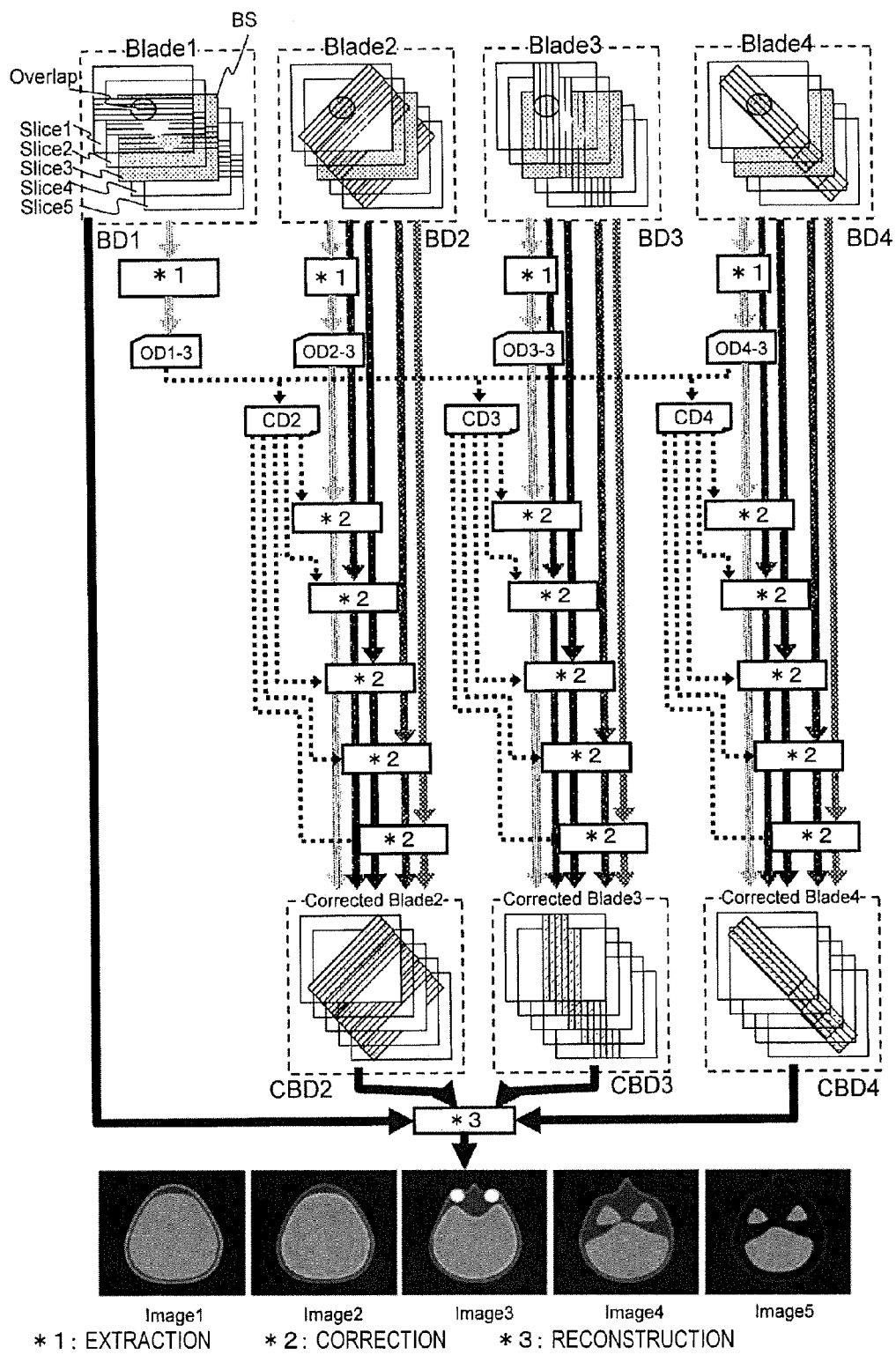
FIG. 9 is a diagram for explaining the flow of correction processing of the first embodiment.

FIG. 9 is a diagram for explaining the flow of correction processing performed by the data correction unit 120 of the present embodiment and image reconstruction processing performed by the image reconstruction unit 130 of the present embodiment. Here, similarly in FIG. 7, a case where the number of slices is 5, the number of blades is 4, and the number of echo signals in each blade is 5 is shown as an example. In addition, it is assumed that each item of blade data is subject to gridding processing in advance when all echo signals in the blade are aligned. However, the gridding processing may also be performed during the correction of the body movement. In addition, similarly in FIG. 7, a number is given to each slice and blade. In addition, the blade 1 (Blade1) is assumed to be a blade as a reference of correction (reference blade).

In addition, the slice 3 (Slice3) is assumed to be a slice as a reference (Benchmark Slice; BS). As this benchmark slice (BS), a slice including a characteristic signal (for example, eyes in the case of head imaging) is desirable so that it is easy to detect rotation translation. The benchmark slice (BS) is set in advance by the operator through the input device 74, for example.

In the blade 1 which is a reference blade, overlap data (Overlap) is extracted from the blade data (BD1-3) of the slice 3 which is a benchmark slice, and this extracted data is set as reference data (OD1-3).

Then, in the blade 2, similarly for the blade 1, overlap data is extracted from blade data (BD2-3) of the benchmark slice (slice 3), and the extracted data is set as object data (OD2-3).

Then, the amount of body movement (the amount of rotation and the amount of translation) of the blade 2 is calculated using the reference data (OD1-3) and the object data (OD2-3). The calculated amount of body movement is stored as correction information 2 (Correction Data 2; CD2) of the blade 2.

Then, the blade data (BD2) of all slices of the blade 2 is corrected for each slice using the correction information 2 (CD2), thereby obtaining corrected blade data of the blade 2 (Corrected Blade2; CBD2). In addition, the correction of each item of the blade data is performed using the above method described in FIG. 8.

Similarly for the blades 3 and 4, overlap data is extracted from the blade data (BD3-3, B04-3) of the benchmark slice, and this is set as object data (OD3-3, OD4-3). Then, correction information 3 (CD3) and correction information 4 (CD4) are calculated using the reference data (OD1-3) and the object data (OD3-3, OD4-3), respectively. Using the correction information 3 (CD3) and the correction information 4 (CD4), the blade data (BD3, BD4) of all slices of the blades 3 and 4 is corrected for each slice. Then, corrected blade data (Corrected Blade3 (CBD3), Corrected Blade4 (CBD4)) of the blades 3 and 4 is obtained.

Then, the image reconstruction unit 130 obtains a reconstructed image (Image1, Image2, Image3, Image4, Image5) by combining the blade data (BD1) of the reference blade and the corrected blade data (CBD2, CBD3, CBD4) for each slice and performing reconstruction processing for each slice.

In the present embodiment, the benchmark slice used in the correction processing is set by the operator. The setting is performed using the input device 74 on the positioning image displayed on the display device 73. Here, a benchmark slice setting screen 400 of the present embodiment configured using a positioning image will be described.

Figure 10:
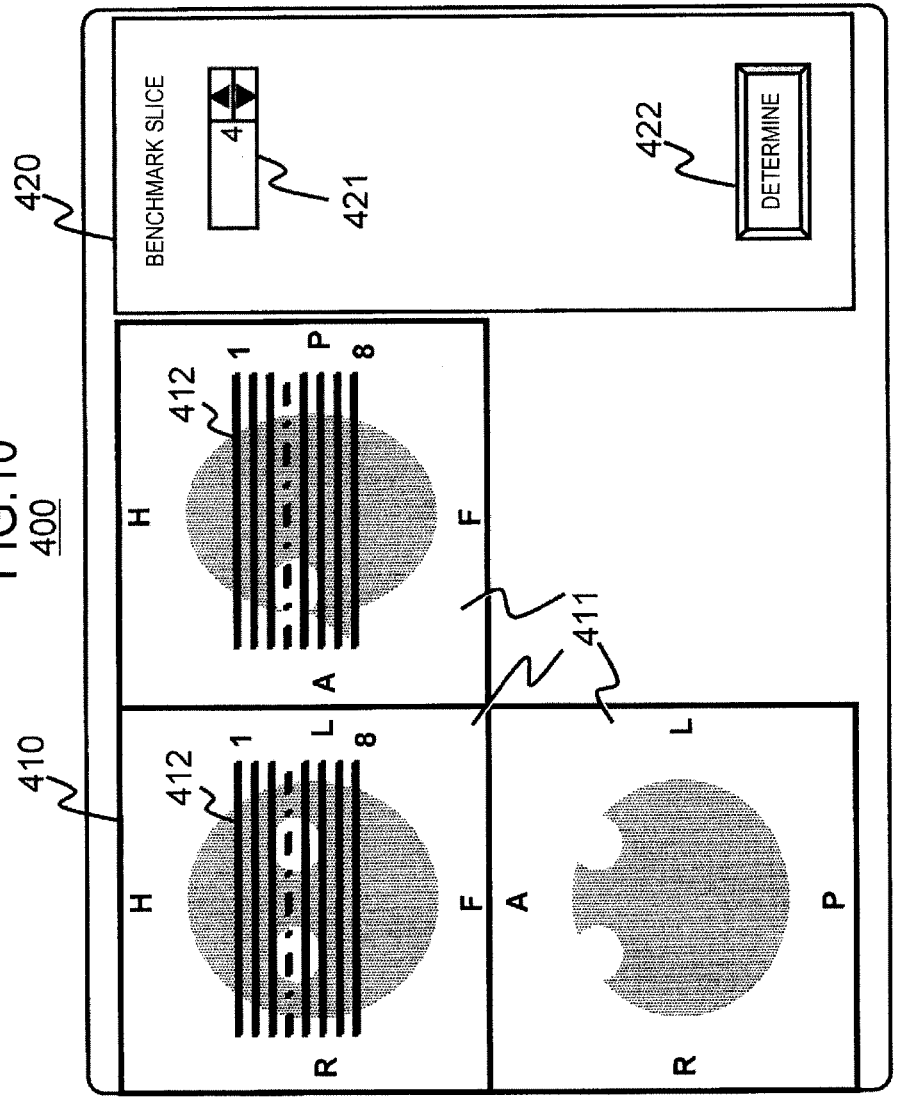
FIG. 10 is an explanatory diagram for explaining a benchmark slice setting screen of the first embodiment.

FIG. 10 is an explanatory view for explaining the benchmark ice setting screen 400 of the present embodiment.

As shown in this drawing, the benchmark slice setting screen 400 of the present embodiment includes an image display portion 410, which displays a positioning image and each slice position of multi-slice imaging, and a number input portion 420 to input the slice number of the benchmark slice.

The number input portion 420 includes a receiving portion 421 to receive an input of a slice number and a determination button 422 to receive the operator's intention to determine the slice input in the receiving portion 421 as a benchmark slice. In addition, the determination button 422 does not need to be independently provided. For example, an imaging start button to receive an instruction to start imaging may also serve as the determination button 422.

Positioning images (an axial image, a coronal image, and a sagittal image) 411 in three directions, a slice number, and a slice position 412 are displayed in the image display portion 410. The slice position 412 shows a slice corresponding to the number, which is input through the number input portion 420, so as to be identifiable.

The operator inputs the slice number in the receiving portion 421, checks the slice displayed in the image display portion 410 visually, and determines the benchmark slice. Alternatively, the slice number displayed in the receiving portion 421 is updated by selecting the slice displayed in the image display portion 410, thereby determining the benchmark slice. The data correction unit 120 receives the slice corresponding to the number, which is input in the receiving portion 421, as a benchmark slice when the determination button 422 is pressed.

Next, the flow of imaging processing of the present embodiment will be described. FIG. 11(*a*) is a process flow for explaining the flow of the imaging processing of the present embodiment. Here, the number of blades is set to K, and the number of slices is set to N. K and N are integers of 1 or more.

When an instruction to start imaging is received, the data collection unit 110 performs data collection processing according to the pulse sequence stored in advance (step S1101). Here, the data collection unit 110 collects echo signals of the number of blades K and the number of slices N, and arranges the echo signals as blade data in k space for each slice and each blade.

Then, the data correction unit 120 performs data correction processing on the blade data of blades other than the reference blade to obtain corrected blade data (step S1102). Details of the data correction processing will be described later.

Then, the image reconstruction unit 130 performs image reconstruction processing (step S1103). Here, the blade data of the reference blade and the corrected blade data of other blades are combined for each slice, and an image is reconstructed from the combined data for each slice.

Here, details of the data correction processing performed by the data correction unit 120 in the above-described step S1102 will be described. FIG. 11(*b*) is a process flow of correction processing of the present embodiment. k and n are a counter of a blade number and a counter of a slice number, respectively. In addition, the slice number of the benchmark slice is set to bs.

First, the data correction unit 120 generates reference data of the benchmark slice bs in a reference blade (in the present embodiment, blade 1). Specifically, the blade number k of the blade to be processed is set to 1 (step S1201). Then, overlap data of the benchmark slice bs is extracted and reference data (OD1-*bs*) is generated (step S1202). The reference data OD1-*bs* is stored in the storage device 72 of the control processing system 70.

Then, the data correction unit 120 acquires correction information for each of blades other than the reference blade and corrects blade data to generate corrected blade data.

Specifically, first, the blade number k of the blade to be processed is set to 2 (step S1203), and then it is determined whether or not processing on all blades has been ended (step S1204).

When there is an unprocessed blade, the data correction unit 120 performs correction information acquisition processing for acquiring correction information k of the blade k (step S1205). Details of the correction information acquisition processing will be described later.

After the correction information k is acquired, the data correction unit 120 corrects the blade data of all slices of the blade k using the correction information k. Here, the slice number n is set to 1 (step S1206). Then, until the processing on all slices is ended (step S1207), body movement correction (step S1208) is repeated using the correction information k (step 1209). In addition, in the body movement correction, corrected blade data is generated and stored for each slice.

Then, after the body movement correction for all slices of the blade k is ended (step S1207), the data correction unit 120 performs the processing of steps S1204 to S1209 for a blade of the next blade number (step S1210). Then, the processing of steps S1204 to S1209 is repeated for each blade until the processing on all blades is ended (step S1204).

Through the above procedure, the data correction unit 120 of the present embodiment obtains the corrected blade data of blades other than the reference blade.

Here, the flow of the correction information acquisition processing performed by the data correction unit 120 in step S1205 will be described. FIG. 11(c) is the process flow of the correction information acquisition processing of the present embodiment.

First, the benchmark slice (slice bs) of the blade to be processed (here, the blade k) is selected (step S1301). Then, overlap data is extracted from blade data (BDk-bs) of the slice be, and the extracted data is set as object data (ODk-bs) (step S1302).

Figure 8:
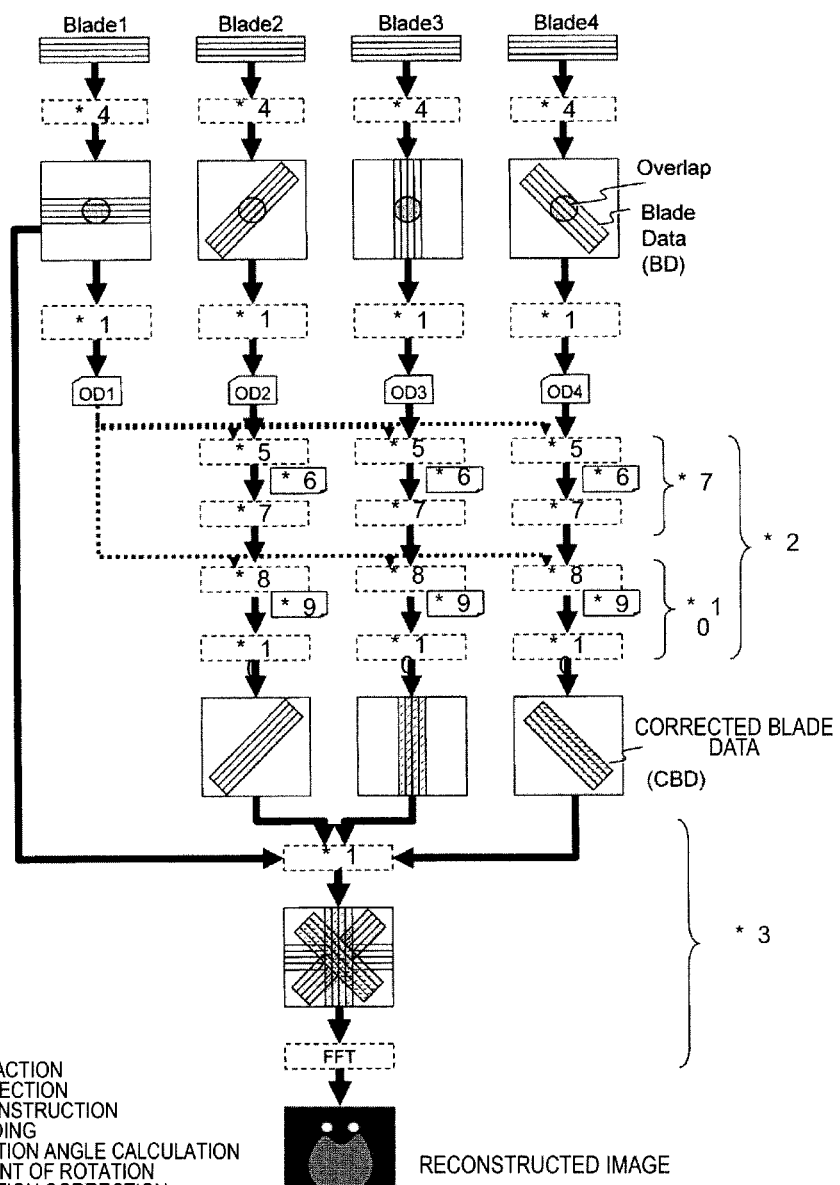
FIG. 8 is an explanatory diagram for explaining the details of body movement correction.

Then, the amount of rotation and the amount of translation are detected from the reference data (OD1-bs) and the object data (ODk-bs), which are obtained in step S1203 of the above-described data correction processing, using the above method described in FIG. 8, and they are set as correction information (CDk) (step S1303).

As described above, according to the present embodiment, other slices are also corrected using the correction information of the benchmark slice. Therefore, compared with a case where correction information is calculated for each slice and body movement correction is performed, it is possible to perform the process at high speed.

For example, when the number of slices is N and the number of blades is K, it is necessary to perform the processing of extracting the overlap data and generating the reference data or the object data (N×K) times and the calculation of correction information (N×(K−1)) times in the general method shown in FIG. 7. In the present embodiment, however, these processes of extracting the overlap data and generating the reference data or the object data and the calculation of correction information may be performed K times and (K−1)) times, respectively. That is, according to the present embodiment, the number of executions of these processes may be reduced by (K×(N−1)) times and ((N−1)×(K−1)) times, respectively. In addition, when using a method of calculating the correction information by performing a Fourier transform of overlap data, the number of times of performing the Fourier transform can be further reduced similarly.

In addition, in the present embodiment, since a slice including the characteristic signal by which rotation or translation can be easily detected is selected as a benchmark slice, the amount of body movement used in the body movement correction can be detected with high accuracy. Therefore, since other slices are also corrected using the amount of body movement detected with high accuracy, it is possible to perform highly accurate body movement correction as a whole. In particular, when the imaging target is a rigid body, such as the head, body movement (rotation, translation) of the object is almost unchanged in any slice. Therefore, the present embodiment is effective when an imaging target is such a part.

Therefore, according to the present embodiment, highly accurate body movement correction can be performed at high speed. That is, according to the present embodiment, it is possible to perform stable body movement correction at high speed regardless of the structure within the imaging cross-section.

Second Embodiment

Next, a second embodiment to which the present invention is applied will be described. The present embodiment is basically the same as the first embodiment, but a benchmark slice is automatically determined. Hereinafter, the present embodiment will be described focusing on the different configuration from the first embodiment.

Figure 12:
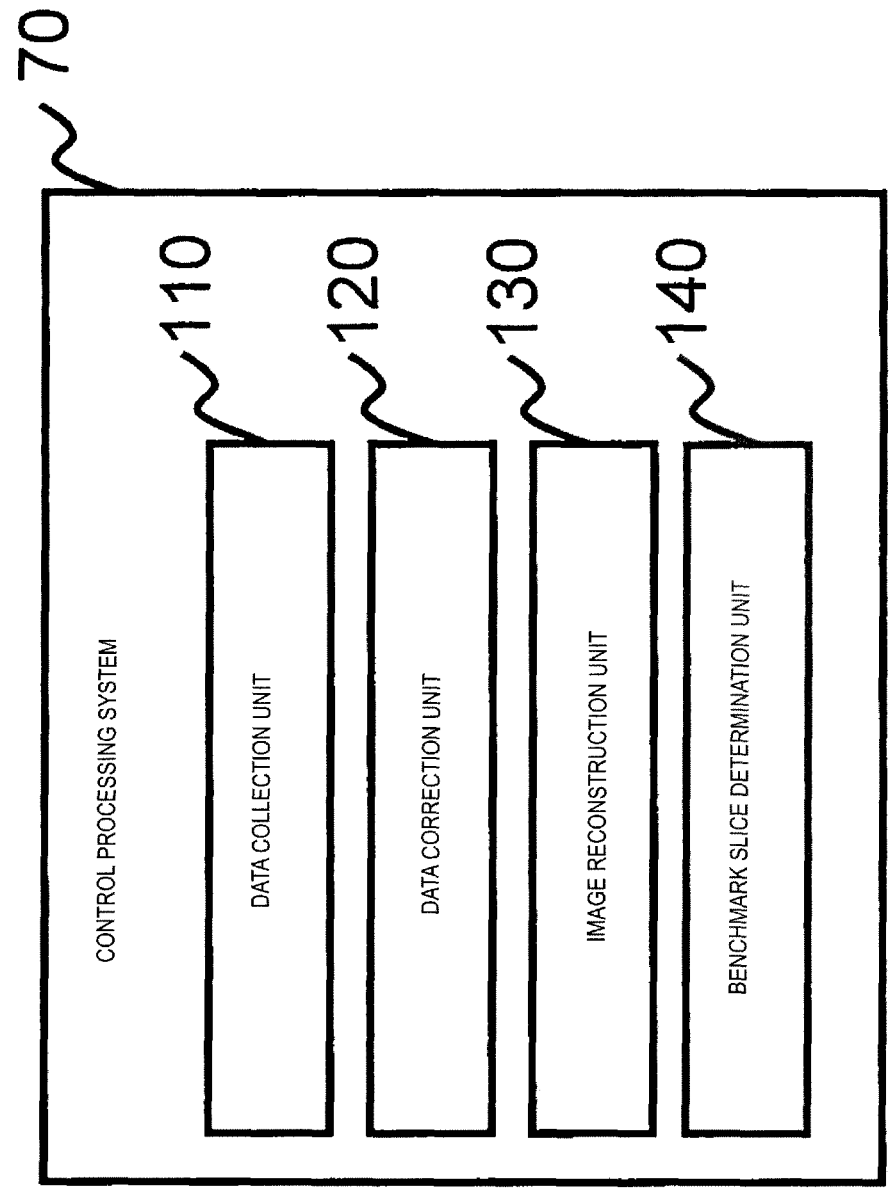
FIG. 12 is a functional block diagram of a control processing system of a second embodiment.

An MRI apparatus 10 of the present embodiment is the same as that of the first embodiment. FIG. 12 shows a functional block diagram of a control processing system 70 of the present embodiment. As shown in this drawing, the control processing system 70 of the present embodiment includes a benchmark slice determination unit 140 in addition to the configuration of the first embodiment.

The benchmark slice determination unit 140 determines a benchmark slice among a plurality of slices. As described above, as the benchmark slice, a slice including a characteristic signal is desirable so that it is easy to detect rotation or translation. In the present embodiment, therefore, the benchmark slice determination unit 140 compares each slice of the reference blade with a rotated image and sets a slice with lowest correlation as a benchmark slice. Hereinafter, details of benchmark slice determination processing of the benchmark slice determination unit 140 of the present embodiment will be described.

Figure 13:
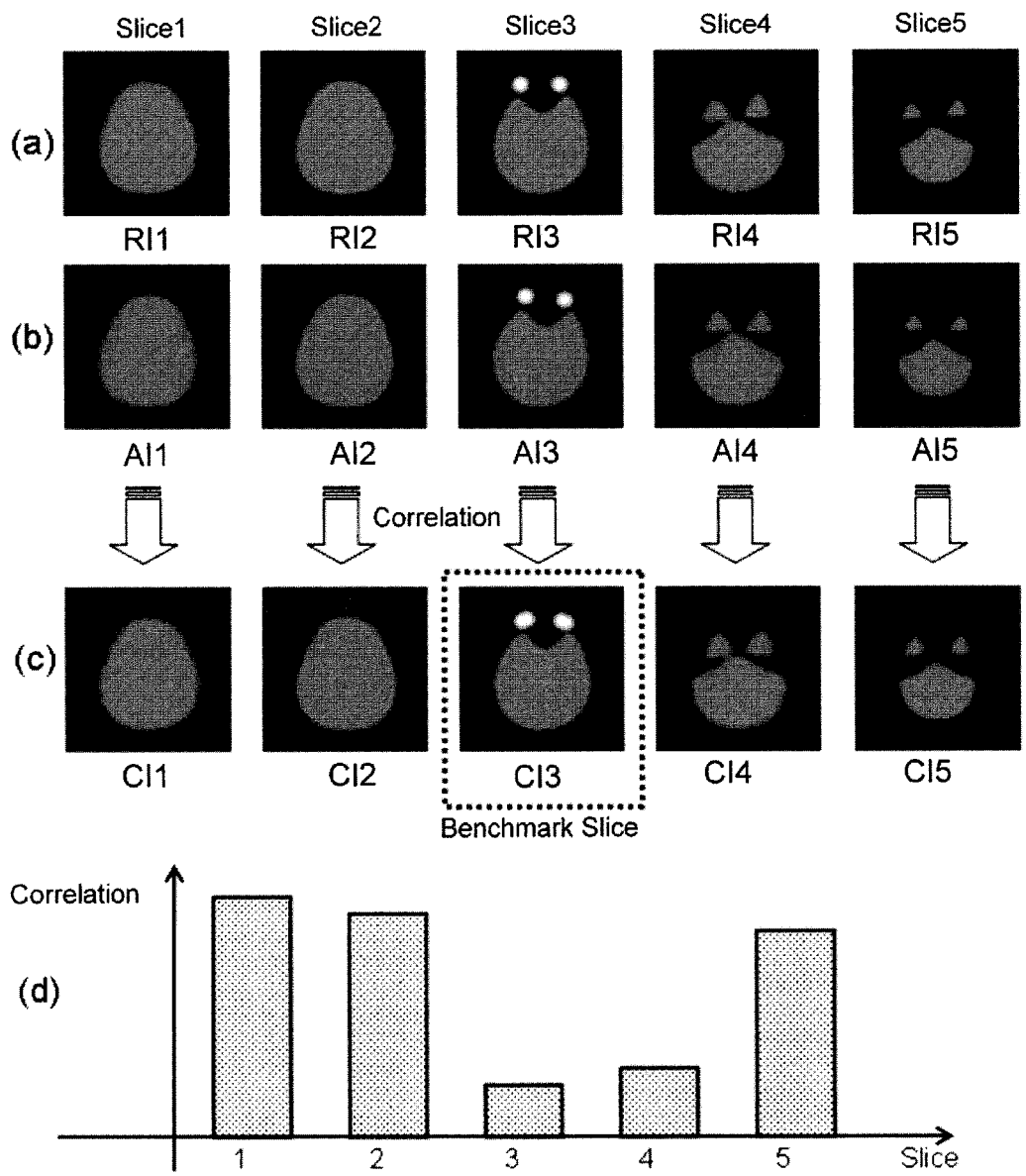
FIGS. 13(a) to 13(d) are explanatory diagrams for explaining benchmark slice determination processing of the second embodiment.

FIG. 13 is a diagram for explaining the details of the benchmark slice determination processing performed by the benchmark slice determination unit 140 of the present embodiment. Here, the number of slices N is set to 5 as an example. In addition, the benchmark slice determination processing is performed using the blade data of the reference blade set in advance.

First, an overlap portion (overlap data) is extracted from the blade data of each slice (Slice1 to Slice5) of the reference blade. Then, a Fourier transform of each item of the extracted overlap data is performed to reconstruct a reference image (RI). FIG. 13(a) shows reconstructed reference images (RI1 to RI5).

Then, processing set in advance is performed on each of the reference images (RI1 to RI5) to generate an applied image (AI). FIG. 13(b) illustrates applied images (AI1 to AI5) obtained by performing processing of rotating the reference images (RI1 to RI5) by 5° clockwise. The processing set in advance is not limited to this, and processing for obtaining an applied image, in which the presence or absence of the characteristic point of each slice can be determined by comparison with the reference image, is also possible.

Then, the correlation between the reference image and the applied image of the same slice is calculated for each slice. For example, the correlation is calculated using a normalized correlation method for calculating the similarity between two items of image data. FIG. 13(c) shows images (CI1 to CI5) of respective slices after correlation processing. In addition, as shown in FIG. 13(d), the correlation processing result may be expressed using the graph of the correlation value between each reference image (RI) and each applied image (AI) corresponding to each other.

The benchmark slice determination unit 140 determines a slice with low similarity, that is, a slice with the lowest correlation value between the reference image (RI) and the applied image (AI) as a benchmark slice. When the object 11 moves rigidly, the same rotation and translation should be detected for each slice. A slice with high sensitivity of correlation processing for this movement can be said to be a slice showing the influence of body movement with high sensitivity. In the present embodiment, therefore, in order to stabilize the correction, a slice with high sensitivity of correlation processing, that is, a slice in which the variation width of the correlation value is largest and the correlation value is lowest is selected and determined as a benchmark slice.

Figure 14:
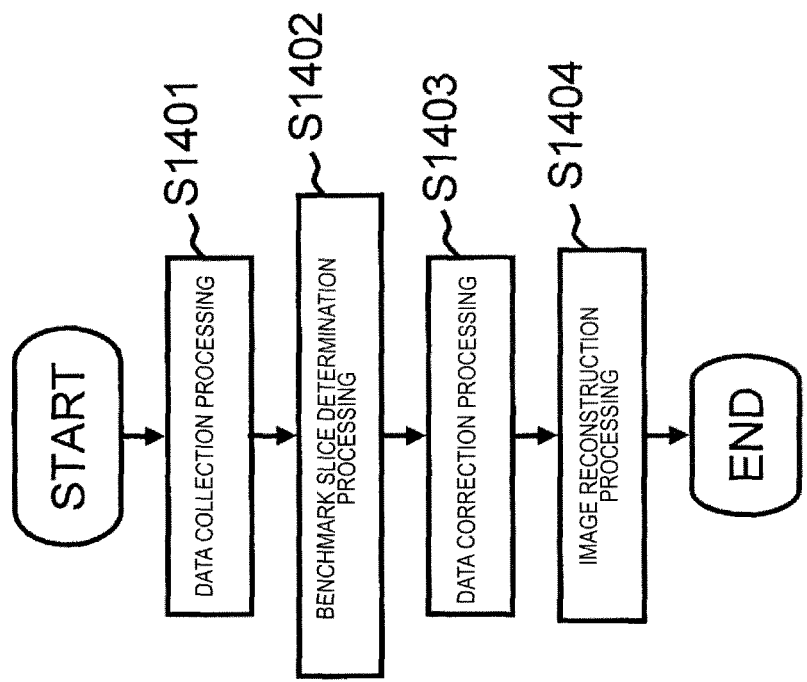
FIG. 14 is a flowchart of imaging processing of the second embodiment.

The flow of imaging processing of the present embodiment will be described. FIG. 14 is a process flow for explaining data correction processing of the imaging processing of the present embodiment.

First, as in the first embodiment, the data collection unit 110 performs data collection processing (step S1401) to acquire blade data (BD) for each blade and each slice.

Then, using the blade data of each slice of the reference blade, the benchmark slice determination unit 140 performs benchmark slice determination processing for determining the benchmark slice using the above-described method (step S1402).

Then, using the benchmark slice determined in step S1402, the data correction unit 120 performs data correction processing on the blade data (BD) of blades other than the reference blade to acquire corrected blade data (CBD) (step S1403). Then, the image reconstruction unit 130 performs image reconstruction processing (step S1404).

In addition, the data correction processing and the correction information acquisition processing of the present embodiment are the same as those of the first embodiment.

As described above, according to the present embodiment, the best slice is automatically selected as a benchmark slice. Since the amount of body movement is calculated and corrected using the benchmark slice, the accuracy of correction is improved. Therefore, according to the present embodiment, correction is further stabilized.

In addition, although the benchmark slice determination unit 140 determines a slice, which shows the influence of body movement with high sensitivity, on the basis of the correlation with an applied image in the present embodiment, the benchmark slice determination method is not limited to this. For example, it is also possible to calculate the distribution of the pixel value of the reference image itself and determine a slice with the largest variance of the pixel values as a benchmark slice.

Third Embodiment

Next, a third embodiment to which the present invention is applied will be described. In each of the embodiments described above, blade data of all blades of all slices is collected in advance (data collection processing), body movement correction is performed thereafter (data correction processing), and corrected blade data is combined to reconstruct an image. In the present embodiment, data collection processing and data correction processing are executed in parallel. Hereinafter, the present embodiment will be described focusing on the different configuration from each of the above embodiments.

The configuration of the MRI apparatus 10 of the present embodiment is basically the same as that of the first embodiment. In addition, the functional configuration of the control processing system 70 of the present embodiment is also the same. In the present embodiment, however, the CPU 71 of the control processing system 70 performs control such that data collection processing of the data collection unit 110 and correction processing of the data correction unit 120 are performed in parallel.

Figure 15:
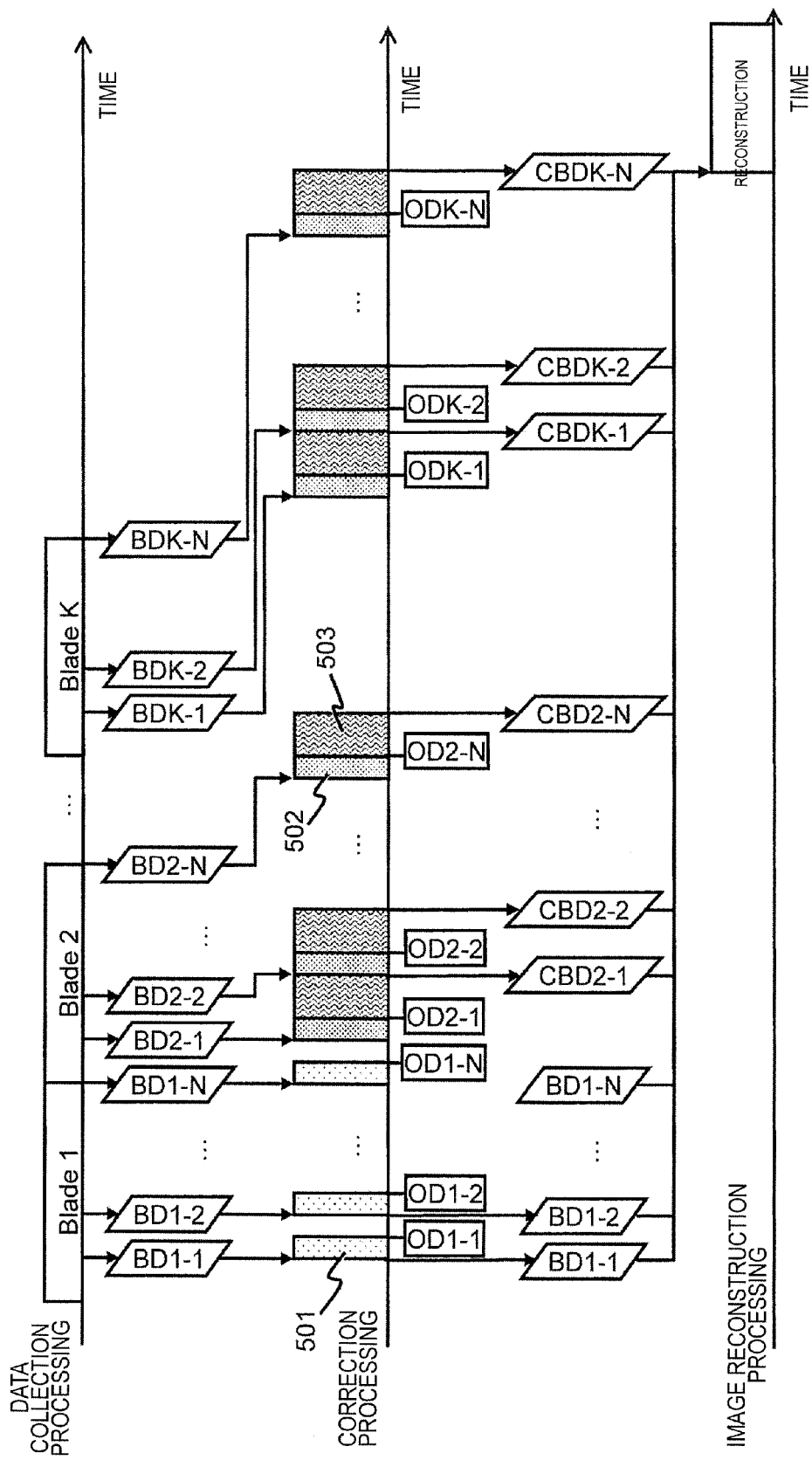
FIG. 15 is an explanatory diagram for explaining the flow of conventional parallel processing.

Prior to explaining the timing of each process of the present embodiment, the timing of each process in the case of performing data collection and correction processing in parallel at the time of multi-slice imaging based on the conventional hybrid radial method will be described with reference to FIG. 15 for comparison. Here, the number of blades is set to K, and the number of slices is set to N. The correction processing is sequentially started whenever the data collection of each slice in one blade ends. The blade 1 is set as a reference blade.

First, as the data collection processing, sequentially from the blade 1, an echo signal is measured sequentially from the slice 1 for each slice. In this case, whenever the measurement of all echo signals of one slice n of the blade k ends, each echo signal is arranged as blade data (BDk-n) in k space.

At the time of data collection processing of the blade 1, whenever each item of the blade data (BD1-n) is arranged in k space, overlap data is extracted and reference data (OD1-n) is generated (reference data generation processing 501).

At the time of data collection processing of other blades, whenever each item of the blade data (BDk-n) is arranged in k space, overlap data is extracted and object data (ODk-n) is generated (object data generation processing 502), the amount of body movement of each slice is detected using the reference data (OD1-n) of the same slice, and corrected blade data (CBDk-n) is generated by correcting the blade data (BDk-n) (body movement amount detection correction processing 503).

After the body movement amount detection correction processing has ended for all slices of all blades, the blade data (BD) of the reference blade and the corrected blade data (CBD) of other blades are combined to reconstruct an image.

The time taken for the conventional parallel processing performed in the above procedure is as follows. Here, the average time taken for the measurement of all echo signals of one slice of one blade is set to $T_{acq}$, the average time required for processing for generating one item of reference data or object data (called OD generation processing) is set to $T_{od}$, and the average time required for the body movement amount detection correction processing for calculating the amount of body movement from the reference data and the object data and correcting the blade data takes is set to $T_{cor}$.

The relationship of the number of blades K, the diameter L of an overlap portion, and the effective matrix M is expressed as in the above-described Expression (1). Since the number of data points (L×M) in one slice of one blade is larger than the number of data points ($\pi L^2/4$) within the overlap portion, the following expression (2) is satisfied.

[Expression 2]

$$T_{od} < T_{acq} \qquad (2)$$

Therefore, time (TotalTime) taken from the start of measurement to the end of correction processing is expressed as in the following expression (3). Here, the time taken from the start of measurement to the end of correction processing changes according to the size relationship between the average time $T_{acq}$ taken for the measurement of all echo signals of one slice of one blade and the sum ($T_{od}+T_{cor}$) of the time taken for OD generation processing and the time taken for correction processing.

[Expression 3]

$$TotalTime = \begin{cases} T_{acq} \times N \times K + T_{od} + T_{cor} & ((T_{od}+T_{cor}) < T_{acq}) \\ T_{acq} \times (N+1) + (T_{od}+T_{cor}) \times N \times (K-1) & ((T_{od}+T_{cor}) < T_{acq}) \end{cases} \qquad (3)$$

Figure 16:
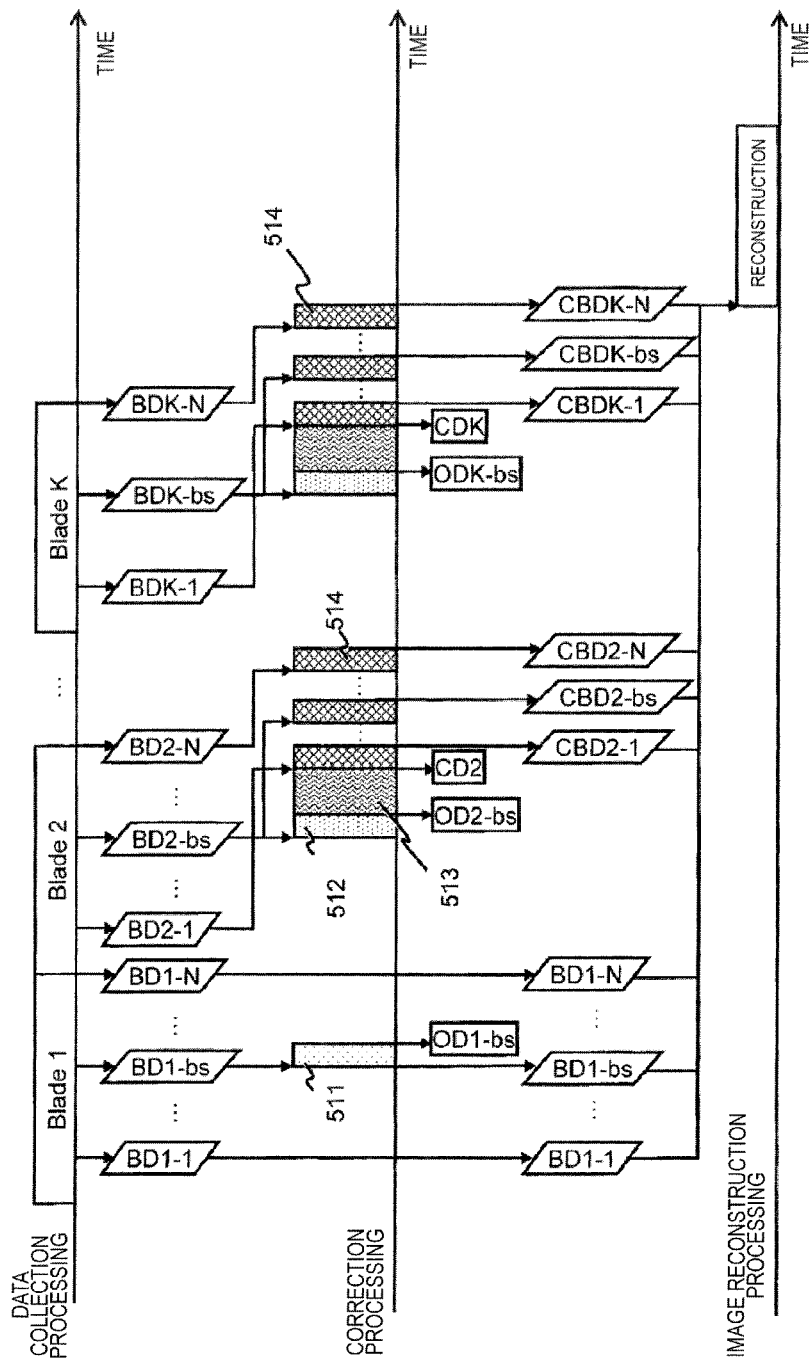
FIG. 16 is an explanatory diagram for explaining the flow of parallel processing of a third embodiment.

Next, the timing of each process of data collection processing, data correction processing, and image reconstruction processing at the time of the multi-slice imaging based on the hybrid radial method of the present embodiment will be described with reference to FIG. 16. Here, similarly in FIG. 15, the number of blades is set to K, and the number of slices is set to N. In addition, as in the first embodiment, it is assumed herein that a benchmark slice (bs-th slice) is determined in advance.

First, the data collection unit 110 performs measurement in order from the blade 1 to the blade K and from the slice 1 to the slice N, and arranges the obtained echo signals as blade data (BDk-n) in k space of each slice of each blade (data collection processing).

While the data collection unit 110 performs the data collection processing, the data correction unit 120 extracts overlap data to generate reference data (OD1-bs) when blade data (BD1-bs) of the slice bs of the blade 1 is arranged in the K space (reference data generation processing 511).

In addition, while the data collection unit 110 performs the data collection processing, the data correction unit 120 extracts overlap data to generate object data (ODk-bs) when blade data (BDk-bs) of the slice bs of the blade k (k is an integer of 2 or more and K or less) is arranged in the k space (object data generation processing 512). Then, correction information (CDk) is generated from the reference data (OD1-bs) and the object data (ODk-bs) (correction information generation processing 513).

After the correction information (CDk) is generated, the data correction unit 120 corrects the blade data (BDk-n) in the order in which the data collection processing has been performed, for a slice of the blade k for which the data collection processing has ended, using the correction information (CDk), thereby generating corrected blade data (CBDk-n) (correction processing 514).

After the data correction unit 120 ends the above-described correction processing until the slice N of the blade K, the image reconstruction unit 130 combines the blade data (BD1-n) of the blade 1 and the corrected blade data (CBDk-n) of other blades for each slice to reconstruct an image for each slice (reconstruction processing).

The time taken for the processing of the present embodiment, which is performed in the above procedure, is as follows. Assuming that the average time required for correction information calculation processing for calculating the correction information is $T_{cd}$ and the average time required for correction processing for correcting each item of blade data using the correction information is $T_{app}$, the following relational expressions (4) is satisfied between $T_{cd}$, $T_{app}$, and $T_{cor}$.

[Expression 4]

$$T_{cd} + T_{app} = T_{cor} \quad (4)$$

In addition, assuming that the average time taken to correct one blade is $T_c$, $T_c$ is expressed as in the following expression (5) using $T_{cd}$, $T_{app}$, and $T_{cor}$.

[Expression 5]

$$T_c = T_{cd} + T_{cor} + T_{app} \times (N-1) \quad (5)$$

Therefore, time taken from the start of measurement to the end of correction processing is expressed as in the following expression (6).

[Expression 6]

$$TotalTime = \begin{cases} T_{acq} \times \{N \times (K-1) + bs\} + T_c & (T_c < T_{acq} \times N) \\ T_{acq} \times (N + bs) + T_c \times (K-1) & (T_c > T_{acq} \times N) \end{cases} \quad (6)$$

Figure 17:
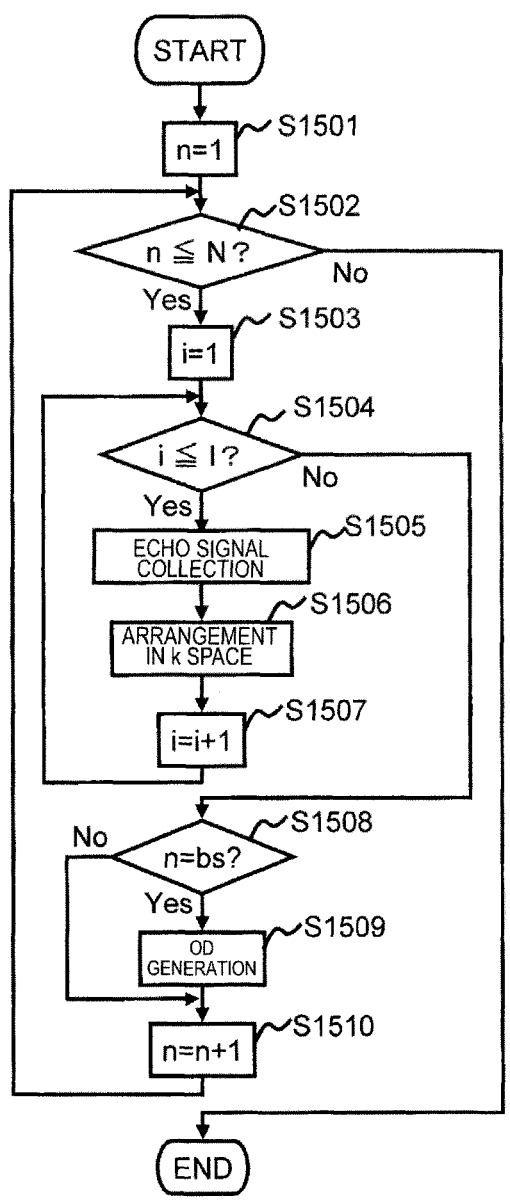
FIG. 17 is a flow chart of OD generation processing of the third embodiment.

Next, the flow of processing (OD generation processing) for generating reference data or object data while collecting echo signals in the present embodiment will be described. FIG. 17 is a process flow for explaining the flow of the OD generation processing of the present embodiment. In this example, echo signals are collected for each slice. Here, the number of slices is set to N, and the number of echo signals acquired in each slice is set to I. In addition, the slice number of the benchmark slice is set to bs.

When an instruction to start aging is received, the data collection unit 110 acquires an echo signal of each slice sequentially from the slice 1 according to the pulse sequence stored in advance, and arranges the echo signal in k space. Whenever the echo signal of each slice is arranged in k space, the data correction unit 120 determines whether or not the slice is a benchmark slice. If the slice is a benchmark slice, the data correction unit 120 generates reference data or contrast data (OD).

Specifically, the data collection unit 110 first substitutes 1 into the slice number counter n (step S1501), and determines whether or not n is equal to or less than N (step S1502). Then, the data collection unit 110 substitutes 1 into the echo number counter i (step S1503), and determines whether or not i is equal to or less than I (step S1504). If i is larger than I, the processing is ended.

On the other hand, if i is equal to or less than I, the data collection unit 110 collects an i-th echo signal (step S1505), and arranges the i-th echo signal in k space (step S1506). Then, i is incremented by 1 (step S1507), and the process proceeds to step S1504.

When the data collection unit 110 ends arranging all echo signals of the slice n in k space of the slice (step S1504), the data correction unit 120 determines whether or not n is bs (step S1509). If n is bs, the data correction unit 120 generates OD (step S1509). Then, n is incremented by 1 (step S1510), and the process returns to step S1502. On the other hand, if n is not bs in step S1508, the process proceeds to step S1510.

The data collection unit 110 and the data correction unit 120 repeat the processing of steps S1502 to S1510 for all slices.

Figure 18:
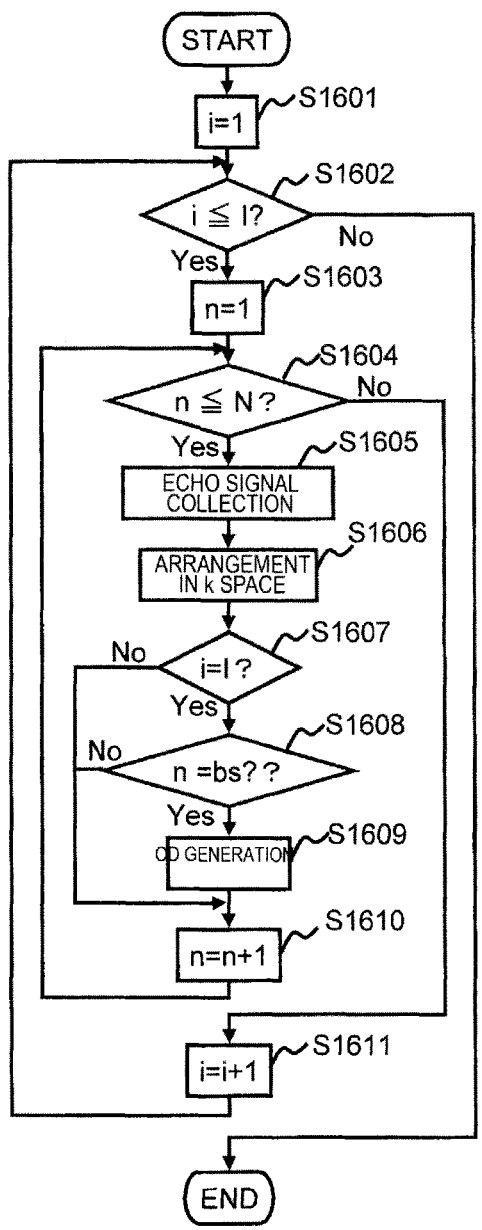
FIG. 18 is a flowchart of another example of OD generation processing of the third embodiment.

FIG. 18 is a process flow for explaining another flow of the OD generation processing of the present embodiment.

Here, echo signals of all slices are collected for each amount of phase encoding. Similarly in FIG. 17, the number of slices is set to N, and the number of echo signals acquired in each slice is set to I. In addition, the slice number of the benchmark slice is set to bs.

In this case, the OD is generated at the timing at which all echo signals of the benchmark slice are collected.

The data collection unit 110 sets the echo number counter i to 1 (step S1601), and determines whether or not i is less than 1 (whether or not i is equal to I) (step S1602).

When i is equal to or less than I, the data collection unit 110 sets the slice number counter n to 1 (step S1603), and determines whether or not n is equal to or less than N (step S1604). When n is equal to or less than N, an i-th echo signal of the n-th slice is collected (step S1605), and is arranged in k space (step S1606).

Here, the data collection unit 110 determines whether or not the collected echo signal is a last echo signal in the slice. That is, it is determined whether or not i is equal to I (step S1607). If the collected echo signal is a last echo signal, the data collection unit 110 determines whether or not the slice is a benchmark slice. That is, it is determined whether or not n is equal to bs (step S1608).

When the data collection unit 110 determines that the last echo signal of the benchmark slice has been acquired, the data correction unit generates OD (step S1609). Otherwise, the data collection unit moves to the next slice (step S1610), and repeats the processing of steps S1604 to S1610 until the collection of all echo signals is completed (step S1611).

As described above, according to the present embodiment, since the body movement correction can be performed in parallel with the data collection, it is possible to increase the processing speed.

Figure 19:
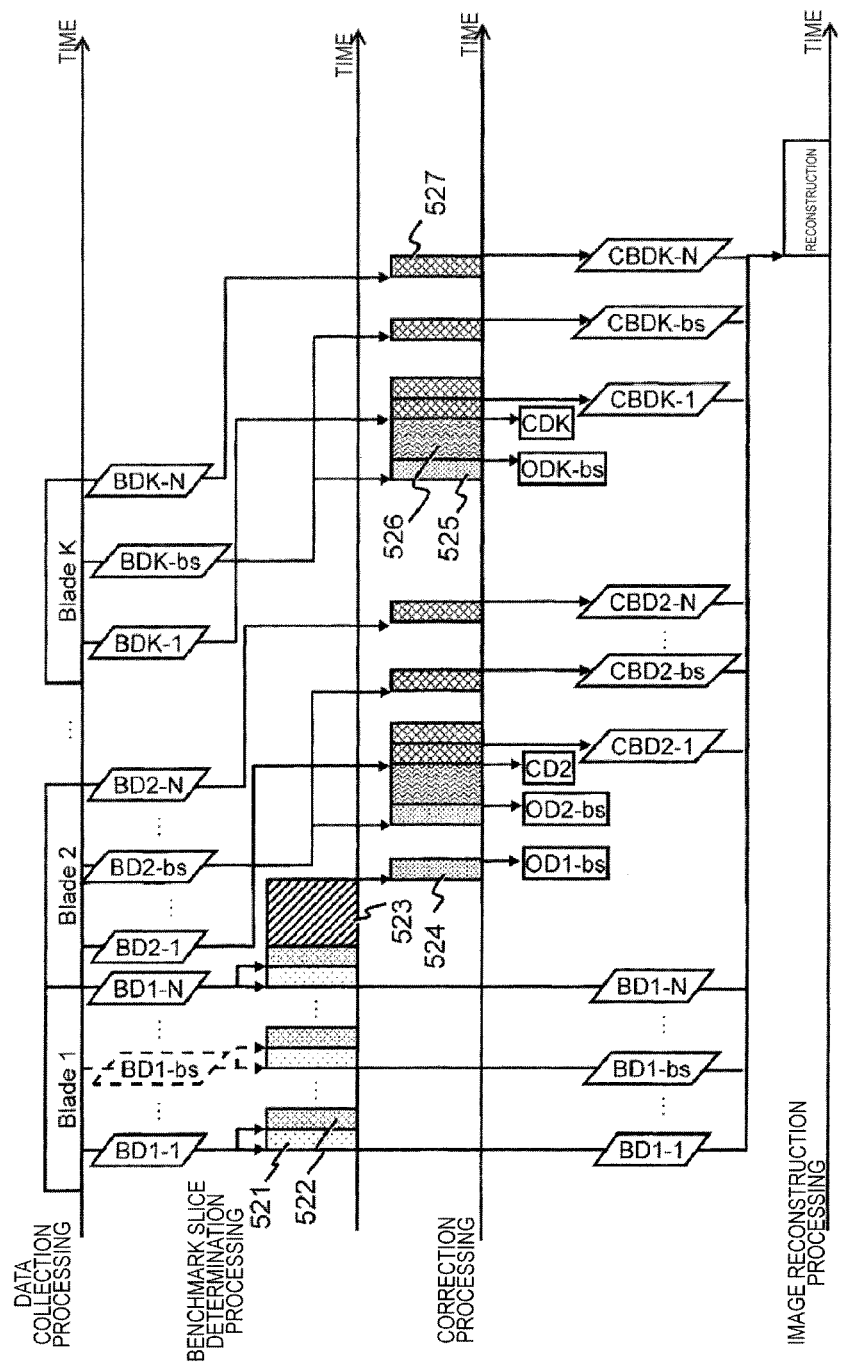
FIG. 19 is an explanatory diagram for explaining another flow of parallel processing of the third embodiment.

In addition, in the present embodiment, a case where the benchmark slice is set in advance as in the first embodiment has been described as an example. However, it is also possible to apply a method of automatically determining the benchmark slice as in the second embodiment. Here, the timing of each process in this case will be described with reference to FIG. 19. Similarly in FIG. 16, the number of blades is set to K, and the number of slices is set to N.

First, the data collection unit 110 performs measurement in order from the blade 1 to the blade K and from the slice 1 to the slice N, and arranges the obtained echo signals as blade data (BDk-n) in k space of each slice of each blade (data collection processing).

While the data collection unit 110 performs the above-described data collection processing, the benchmark slice determination unit 140 performs reference image generation processing 521, which is for extracting overlap data and reconstructing a reference image (RI), and applied image generation processing 522, which is for generating an applied image (AI) from the reference image, for each slice of the blade 1 whenever the blade data (BD1-n) is obtained.

After the generation of reference images and applied images of all slices of the blade 1 is ended, the benchmark slice determination unit 140 performs correlation processing 523 for determining the benchmark slice from the correlation between the reference image and the applied image of each slice (benchmark slice determination processing). In addition, whenever the reference image and the applied image of each slice are obtained, the correlation between both the reference image and the applied image may be calculated, so that only the selection is performed in the correlation processing 523.

After the benchmark slice determination unit 140 determines the benchmark slice bs, the data correction unit 120 performs reference data generation processing 524 for generating the reference data (OD1-bs) from the blade data of the benchmark slice bs of the blade 1.

Then, when the blade data (BDk-bs) of the slice bs of the blade k is arranged in the k space, the data correction unit 120 performs object data generation processing 525 for generating the object data (ODk-bs) and performs correction information generation processing 526 for generating the correction information (ODk) from the reference data (OD1-bs) and the object data (ODk-bs).

After the correction information (CDk) is generated, the data correction unit 120 corrects the blade data (BDk-n) in order in which the data collection processing has been performed, for a slice of the blade k for which the data collection processing has ended, using the correction information (CDk), and performs correction processing 527 for generating the corrected blade data (CBDk-n).

After the data correction unit 120 ends the above-described correction processing up to the slice N of the blade K, the image reconstruction unit 130 combines the blade data (BD1-n) of the blade 1 and the corrected blade data (CBDk-n) of other blades for each slice to reconstruct an image for each slice (reconstruction processing).

As described above, the accuracy of correction can be improved by determining the benchmark slice automatically and calculating the correction information. In addition, it is possible to increase the processing speed by performing the data collection processing and the correction processing in parallel.

In addition, although the case where the multi-slice imaging is performed using a two-dimensional hybrid radial method and the data of the three-dimensional region is collected has been described as the example in each of the above embodiments, the imaging is not limited to this. For example, as shown in FIG. 20, it is also possible to collect the data of the three-dimensional region using a three-dimensional hybrid radial method.

Figure 20:
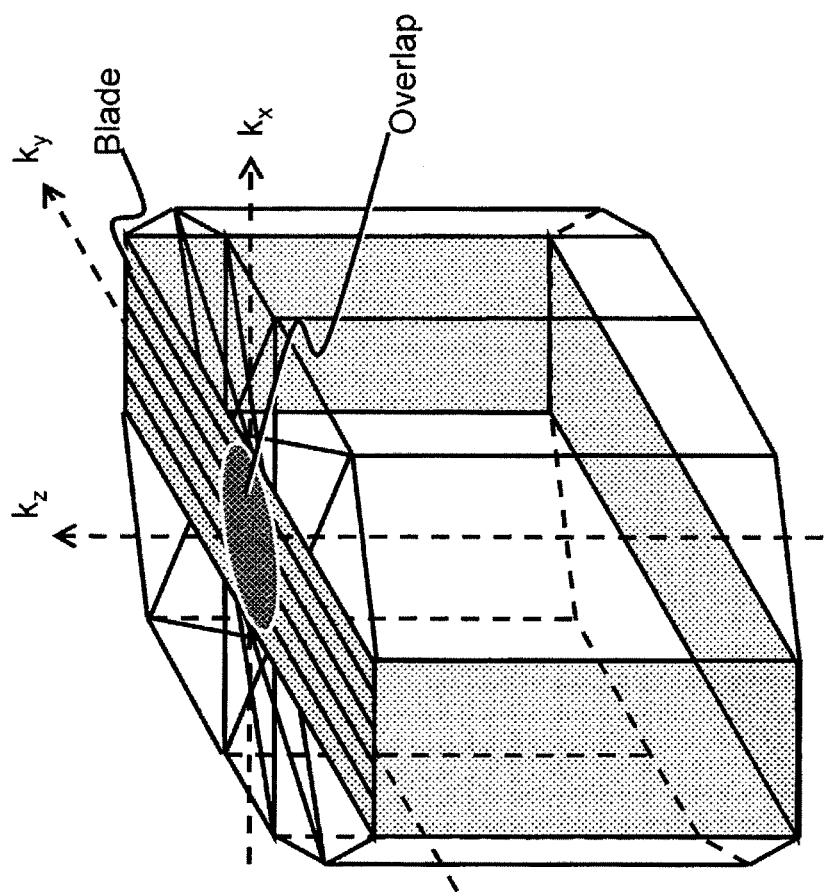
FIG. 20 is an explanatory diagram for explaining how to collect echo signals of a three-dimensional region using the hybrid radial method.

In FIG. 20, kz indicates a slice encoding direction, and kx and ky indicate two perpendicular directions within the plane perpendicular to kz. In the three-dimensional hybrid radial method, sampling according to the two-dimensional hybrid radial method within the kx-ky plane is performed by the number of slice encoding in the kz direction.

In this case, in order to apply the body movement correction of each of the above embodiments, a Fourier transform is first performed on the collected data in the slice encoding direction (kz direction). As a result, multi-slice blade data is obtained. The body movement correction processing of each of the above embodiments is applied to the data after the Fourier transform (multi-slice blade data). In this manner, even if echo signals are collected using the three-dimensional hybrid radial method, the same effects as in each of the above embodiments can be obtained.

In addition, although the blade 1 is used as a reference blade in each of the above embodiments, the reference blade is not limited to this. The reference blade may be arbitrarily selected by the operator. The selection of the reference blade may also be performed using the above-described slice selection screen 400.

In addition, although the case where the hybrid radial method is used as a sampling method of k space has been described as an example in each of the above embodiments, the sampling method is not limited to this. It is preferable that a desired region of k space be repeatedly sampled. Therefore, it is also possible to apply the spiral method as described above. In the case of the spiral method, the above-described processing is performed using the data of the overlap region for each interleave instead of the blade of the hybrid radial method described above.

In addition, although the data correction unit 120 is provided in the control processing system 70 in the above explanation of each embodiment, the present invention is not limited to this. An external information processing apparatus that can transmit and receive data to and from the MRI apparatus 10 may include the data correction unit 120. In addition, the same is true for the benchmark slice determination unit 140 of the second and third embodiments.

In addition, the calculation of the correction information including the amount of rotation and the amount of translation is not limited to the above-described method. For example, overlap data of the benchmark slice of the reference blade is reconstructed, and templates for detecting the rotation and the translation from the reconstructed image are generated. Templates obtained by changing the variation ($\Delta\theta$, ($\Delta x$, $\Delta y$)) set in advance in the expected movement range of the object is generated. Then, matching between these templates and an image reconstructed from the overlap data of the benchmark slice of other blades is formed, and the amount of rotation and the amount of translation specified by the template with largest correlation are set as the amount of rotation and the amount of translation to be applied.

The features of the present invention that has been apparent from the explanation of each of the above embodiments of the present invention can be summarized as follows.

That is, an MRI apparatus of the present invention acquires an image of each slice of an object on the basis of magnetic resonance signals measured from a plurality of slices of the object arranged in a static magnetic field, and includes: a data collection unit that collects a magnetic resonance signal corresponding to each specific region as specific region data by rotating a specific region, which includes an origin of k space and a vicinity of the origin, around the origin; a data correction unit that corrects the specific region data to generate corrected specific region data; and an image reconstruction unit that reconstructs an image from the corrected specific region data. The data correction unit sets one of the plurality of slices as a benchmark slice, detects body movement of the object, which occurs between measurement of a reference specific region as a reference of the plurality of specific regions and measurement of other specific regions excluding the reference specific region, in the benchmark slice, corrects specific region data of the other specific regions in all slices so as to eliminate an influence of the detected body movement on an image, and sets specific region data of the reference specific region and specific region data after correction of the other specific regions as the corrected specific region data in each slice.

Preferably, the data correction unit calculates the body movement in a benchmark slice using data of an overlap region of the reference specific region and the other specific regions.

In addition, preferably, the data correction unit includes a benchmark slice determination unit that determines the benchmark slice, and the benchmark slice determination unit determines a slice of which a predetermined feature amount is maximum or minimum, among all slices, as the benchmark slice.

In addition, preferably, the benchmark slice determination unit determines a slice with a smallest correlation between an image reconstructed from data of an overlap region of the reference specific region and the other specific regions and a test image generated using a method set in advance, among all slices, as the benchmark slice.

In addition, preferably, the benchmark slice determination unit determines a slice whose variance of pixel value distribution of en image reconstructed from data of an overlap region of the reference specific region and the other specific regions is largest, among all slices, as the benchmark slice.

In addition, preferably, whenever the data collection unit collects the specific region data, the data correction unit corrects the specific region data.

In addition, preferably, an image of each of the slices is obtained by performing a Fourier transform, of three-dimensional volume data in a slice direction.

In addition, preferably, a receiving unit that receives designation of the benchmark slice from an operator is provided, and the data correction unit performs the correction with a slice received in the receiving unit as the benchmark slice.

In addition, preferably, the receiving unit includes an image display region where positions of the plurality of slices are displayed on positioning images and a designation region for designating a slice, and the slice designated in the designation region is splayed so as to be identifiable in the image display region.

In addition, preferably, each specific region has a plurality of trajectories parallel to a measurement trajectory passing through the origin.

In addition, a magnetic resonance imaging method of the present invention acquires an image of each slice of an object on the basis of magnetic resonance signals measured from a plurality of slices of the object arranged in a static magnetic field. The magnetic resonance imaging method includes: a data collection step of collecting a magnetic resonance signal corresponding to each specific region as specific region data by rotating a specific region, which includes an origin of k space and a vicinity of the origin, around the origin; a data correction step of correcting the specific region data to generate corrected data; and an image reconstruction step of reconstructing an image from the corrected data. The data correction step includes a correction information calculation step of calculating as correction information an amount of body movement of the object, which occurs between measurement of a reference specific region as a reference of the plurality of specific regions and measurement of other specific regions excluding the reference specific region, in a benchmark slice as a reference and a correction step of correcting data of the other specific regions for all slices using the calculated correction information of each of the other specific regions.

Preferably, the correction information calculation step is executed whenever measurement of the benchmark slice in each specific region is ended.

In addition, preferably, the correction step is executed whenever the correction information of each specific region is calculated in the correction information calculation step.

REFERENCE SIGNS LIST

10: MRI apparatus
11: object
20: static magnetic field generation system
30: gradient magnetic field generation system
31: gradient magnetic field coil
32: gradient magnetic field power source
40: sequencers
50: signal transmission system
51: transmission coil
52: synthesizer
53: modulator
54: high frequency amplifier
60: signal receiving system
61: receiving coil
62: signal amplifier
63: quadrature phase detector
64: AD converter
70: control processing system
71: CPU
72: storage device
73: display device
74: input device
110: data collection unit
120: data correction unit
130: image reconstruction unit
140: benchmark slice determination unit
200: pulse sequence
201: excitation RE pulse
203: reverse RE pulse
211: slice selection gradient magnetic field pulse
212: slice re-phase pulse
213: slice selection gradient magnetic field pulse
223: first readout gradient magnetic field pulse
231: readout dephase gradient magnetic field pulse
233: second readout gradient magnetic field pulse
243: sampling window
253: echo signal
261: time interval
310: blade
320: central angle
330: overlap portion
400: benchmark slice setting screen 410: image display portion
411: positioning image
412: slice position
420: number input portion
421: receiving portion
422: determination button
501: reference data generation processing
502: object data generation processing
503: body movement amount detection correction processing
511: reference data generation processing
512: object data generation processing
513: correction information generation processing
514: correction processing
521: reference image generation processing
522: applied image generation processing
523: correlation processing
524: reference data generation processing
525: object data generation processing
526: correction information generation processing
527: correction processing

The invention claimed is:

1. A magnetic resonance imaging apparatus that acquires an image of each slice of an object on the basis of magnetic resonance signals measured from a plurality of slices of the object arranged in a static magnetic field, the apparatus comprising:
a data collection unit that collects a magnetic resonance signal corresponding to each specific region amongst a plurality of specific regions, as specific region data, by rotating a specific region, which includes an origin of k space and a vicinity of the origin, around the origin;
a data correction unit that corrects the specific region data to generate corrected specific region data; and
an image reconstruction unit that reconstructs an image from the corrected specific region data,
wherein the data correction unit sets one of the plurality of slices as a benchmark slice, detects body movement of the object, which occurs between measurement of a reference specific region as a reference of the plurality of specific regions and measurement of other specific regions excluding the reference specific region, in the benchmark slice, corrects specific region data of the other specific regions in all slices so as to eliminate an influence of the detected body movement on an image, and sets specific region data of the reference specific region and specific region data after correction of the other specific regions as the corrected specific region data in each slice,
wherein the data correction unit includes a benchmark slice determination unit that determines the benchmark slice, and
the benchmark slice determination unit determines a slice of which a predetermined feature amount is maximum or minimum, among all slices, as the benchmark slice.

2. The magnetic resonance imaging apparatus according to claim 1,
wherein the data correction unit calculates the body movement in a benchmark slice using data of an overlap region of the reference specific region and the other specific regions.

3. The magnetic resonance imaging apparatus according to claim 1,
wherein the benchmark slice determination unit determines a slice with a smallest correlation between an image reconstructed from data of an overlap region of the reference specific region and the other specific regions and a test image generated using a method set in advance, among all slices, as the benchmark slice.

4. The magnetic resonance imaging apparatus according to claim 1,
wherein the benchmark slice determination unit determines a slice whose variance of pixel value distribution of an image reconstructed from data of an overlap region of the reference specific region and the other specific regions is largest, among all slices, as the benchmark slice.

5. The magnetic resonance imaging apparatus according to claim 1,
wherein, whenever the data collection unit collects the specific region data, the data correction unit corrects the specific region data.

6. The magnetic resonance imaging apparatus according to claim 1,
wherein an image of each of the slices is obtained by performing a Fourier transform of three-dimensional volume data in a slice direction.

7. The magnetic resonance imaging apparatus according to claim 1, further comprising:
a receiving unit that receives designation of the benchmark slice from an operator,
wherein the data correction unit performs the correction with a slice received in the receiving unit as the benchmark slice.

8. The magnetic resonance imaging apparatus according to claim 7,
wherein the receiving unit includes an image display region where positions of the plurality of slices are displayed on positioning images and a designation region for designating a slice, and
the slice designated in the designation region is displayed so as to be identifiable in the image display region.

9. The magnetic resonance imaging apparatus according to claim 1,
wherein each specific region has a plurality of trajectories parallel to a measurement trajectory passing through the origin.

10. A magnetic resonance imaging method of acquiring an image of each slice of an object on the basis of magnetic resonance signals measured from a plurality of slices of the object arranged in a static magnetic field, the method comprising:
a data collection step of collecting a magnetic resonance signal corresponding to each specific region amongst a plurality of specific regions, as specific region data by rotating a specific region, which includes an origin of k space and a vicinity of the origin, around the origin;
a data correction step of correcting the specific region data to generate corrected data; and
an image reconstruction step of reconstructing an image from the corrected data,
wherein the data correction step includes a correction information calculation step of calculating as correction information an amount of body movement of the object, which occurs between measurement of a reference specific region as a reference of the plurality of specific regions and measurement of other specific regions excluding the reference specific region, in a benchmark slice as a reference and a correction step of correcting data of the other specific regions for all slices using the calculated correction information of each of the other specific regions, wherein the data correction step includes a benchmark slice determination step that determines the benchmark slice, and the benchmark slice determination step determines a slice of which a predetermined feature amount is maximum or minimum, among all slices, as the benchmark slice.

11. The magnetic resonance imaging method according to claim 10, wherein the correction information calculation step is executed whenever measurement of the benchmark slice in each specific region is ended.

12. The magnetic resonance imaging method according to claim 11, wherein the correction step is executed whenever the correction information of each specific region is calculated in the correction information calculation step.

* * * * *